(12) United States Patent
Loury et al.

(10) Patent No.: US 8,603,521 B2
(45) Date of Patent: Dec. 10, 2013

(54) FORMULATIONS OF HISTONE DEACETYLASE INHIBITOR AND USES THEREOF

(75) Inventors: David J. Loury, San Jose, CA (US); Joseph J. Buggy, Mountain View, CA (US); Tarak D. Mody, Sunnyvale, CA (US); Erik J. Verner, Belmont, CA (US); Norbert Purro, Los Gatos, CA (US); Sriram Balasubramanian, San Carlos, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 272 days.

(21) Appl. No.: 12/761,588

(22) Filed: Apr. 16, 2010

(65) Prior Publication Data

US 2011/0311624 A1 Dec. 22, 2011

Related U.S. Application Data

(60) Provisional application No. 61/170,517, filed on Apr. 17, 2009.

(51) Int. Cl.
*A61K 9/22* (2006.01)

(52) U.S. Cl.
USPC ........... 424/457; 424/464; 424/465; 514/320; 514/575

(58) Field of Classification Search
USPC .................... 424/464, 465; 514/320, 575
See application file for complete search history.

(56) References Cited

U.S. PATENT DOCUMENTS

| | | |
|---|---|---|
| 2,789,118 A | 4/1957 | Bernstein et al. |
| 2,990,401 A | 6/1961 | Bernstein et al. |
| 3,048,581 A | 8/1962 | Fried |
| 3,126,375 A | 3/1964 | Ringold et al. |
| 3,749,712 A | 7/1973 | Cavazza et al. |
| 3,928,326 A | 12/1975 | Brattsand et al. |
| 3,929,768 A | 12/1975 | Brattsand et al. |
| 3,996,359 A | 12/1976 | Brattsand et al. |
| 4,871,549 A | 10/1989 | Ueda et al. |
| 5,011,692 A | 4/1991 | Fujioka et al. |
| 5,017,381 A | 5/1991 | Maruyama et al. |
| 5,229,135 A | 7/1993 | Philippon et al. |
| 5,260,068 A | 11/1993 | Chen |
| 5,260,069 A | 11/1993 | Chen |
| 5,508,040 A | 4/1996 | Chen |
| 5,567,441 A | 10/1996 | Chen |
| 5,612,059 A | 3/1997 | Cardinal et al. |
| 5,698,220 A | 12/1997 | Cardinal et al. |
| 5,798,119 A | 8/1998 | Herbig et al. |
| 5,837,284 A | 11/1998 | Mehta et al. |
| 5,840,329 A | 11/1998 | Bai |
| 7,276,612 B2 | 10/2007 | Verner et al. |
| 2004/0132825 A1 * | 7/2004 | Bacopoulos et al. ......... 514/575 |
| 2007/0293540 A1 * | 12/2007 | Verner et al. .................. 514/320 |
| 2008/0153877 A1 | 6/2008 | Adimoolam et al. |
| 2011/0039840 A1 | 2/2011 | Varasi et al. |
| 2011/0065734 A1 | 3/2011 | Bar et al. |

FOREIGN PATENT DOCUMENTS

| | | |
|---|---|---|
| WO | WO-2004-092115 A2 | 10/2004 |
| WO | WO-2004-092115 A3 | 10/2004 |
| WO | WO-2005-097770 A1 | 10/2005 |
| WO | WO-2008-082856 A1 | 7/2008 |

OTHER PUBLICATIONS

PCT/US2011/051470 International Search Report and Written Opinion dated Sep. 13, 2011.

\* cited by examiner

*Primary Examiner* — Michael G Hartley
*Assistant Examiner* — Micah-Paul Young
(74) *Attorney, Agent, or Firm* — Wilson, Sonsini, Goodrich & Rosati

(57) ABSTRACT

Dosing regimens, methods of treatment, controlled release formulations, and combination therapies that include an HDAC inhibitor, or a pharmaceutically acceptable salt thereof, are described.

13 Claims, 2 Drawing Sheets

Modeling Dose Schedules

Continuous, IV or Oral dosing for 2 days : Compound 1 at 2mg/kg

FORMULATIONS OF HISTONE DEACETYLASE INHIBITOR AND USES THEREOF

RELATED APPLICATIONS

This application claims benefit of U.S. Provisional Application No. 61/170,517, entitled "ORAL FORMULATIONS OF HISTONE DEACETYLASE INHIBITOR" filed on Apr. 17, 2009, which is herein incorporated by reference.

FIELD OF THE INVENTION

Pharmaceutical compositions are described that include a histone deacetylase (HDAC) inhibitor compound for the treatment of cancer. Methods of treatment using the pharmaceutical compositions and dosing regimens are also described.

BACKGROUND OF THE INVENTION

The acetylation state of nucleosomal histones plays an important role in the regulation of gene expression. Deacetylation of nucleosomal histones is catalyzed by a group of enzymes known as histone deacetylases (HDACs), of which there are eleven known isoforms. Histone deacetylation leads to chromatin condensation resulting on transcriptional repression, whereas acetylation induces localized relaxation within specific chromosomal regions to allow better access to transcriptional machinery to facilitate transcription.

In tumor cells, selective inhibitors of HDAC enzymes leads to histone hyperacetylation. This alters the transcriptional regulation of a subset of genes, including many tumor suppressors, genes involved in cell cycle control, cell division and apoptosis. Further, HDAC inhibitors have been reported to inhibit tumor growth in vivo. The inhibition of tumor growth is accompanied by histone and tubulin hyperacetylation and may involve multiple mechanisms.

HDAC inhibitors block cancer cell proliferation both in vitro and in vivo. N-hydroxy-4-{2-[3-(N,N-dimethylaminomethyl)benzofuran-2-ylcarbonylamino]ethoxy}-benzamide (Compound 1) is a hydroxamate-based HDAC inhibitor for use in the treatment of cancer in a human.

SUMMARY OF THE INVENTION

Pharmaceutical compositions, methods of treating cancer, dosing regimens and combination therapies are disclosed. In one aspect, described is a method of treating cancer in a human comprising: administering to the human a pharmaceutical composition comprising an histone deacetylase (HDAC) inhibitor in cycles consisting of 5 to 9 consecutive days of daily administration of the pharmaceutical composition comprising the HDAC inhibitor followed by 2 to 7 consecutive days with no administration of the pharmaceutical composition comprising the HDAC inhibitor. In some embodiments, the method of treating cancer in a human comprises: administering to the human a pharmaceutical composition comprising an histone deacetylase (HDAC) inhibitor in cycles consisting of 5 to 9 consecutive days of daily administration of the pharmaceutical composition comprising the HDAC inhibitor followed by 5 to 7 consecutive days with no administration of the pharmaceutical composition comprising the HDAC inhibitor In some embodiments, the 5 to 9 consecutive days of daily administration of the pharmaceutical composition comprising the HDAC inhibitor comprises: daily administration of two immediate release pharmaceutical compositions comprising the HDAC inhibitor, wherein the two immediate release pharmaceutical compositions are administered consecutively with the second immediate release pharmaceutical composition being administered about 4 to about 6 hours form the first immediate release pharmaceutical compositions; or daily administration of a single controlled release oral solid dosage pharmaceutical composition comprising the HDAC inhibitor.

In some embodiments, the 5 to 9 consecutive days of daily administration of the pharmaceutical composition comprising the HDAC inhibitor comprises daily administration of the HDAC inhibitor in sufficient amount to maintain effective plasma concentrations of the HDAC inhibitor in the human for at least about 6 consecutive hours on the days of dosing. In some embodiments, the 5 to 9 consecutive days of daily administration of the pharmaceutical composition comprising the HDAC inhibitor comprises daily administration of the HDAC inhibitor in sufficient amount to maintain effective plasma concentrations of the HDAC inhibitor in the human for at least about 6 consecutive hours on the days of dosing but not exceeding 14 consecutive hours.

In some embodiments, the 5 to 9 consecutive days of daily administration of the pharmaceutical composition comprising the HDAC inhibitor comprises daily administration of the HDAC inhibitor in sufficient amount to maintain effective plasma concentrations of the HDAC inhibitor in the human for about 6 consecutive hours to about 8 consecutive hours on the days of dosing.

In some embodiments, the 5 to 9 consecutive days of daily administration of the pharmaceutical composition comprising the HDAC inhibitor comprises: daily administration of two immediate release pharmaceutical compositions comprising the HDAC inhibitor, wherein the two immediate release pharmaceutical compositions are administered consecutively 4 to 6 hours apart; or daily administration of a single controlled release oral solid dosage pharmaceutical composition comprising the HDAC inhibitor.

In some embodiments, the single controlled release oral solid dosage pharmaceutical composition comprising the HDAC inhibitor provides substantially the same in vivo release in the human as two immediate release pharmaceutical compositions comprising the HDAC inhibitor administered consecutively 4 to 6 hours apart.

In some embodiments, the HDAC inhibitor is: N-hydroxy-4-[2-(4-methoxyquinolin-2-ylcarbonylamino)ethoxy]benzamide; N-hydroxy-4-[2S-(trans-cinnamoylamino)butoxy]benzamide; N-hydroxy-4-[2R-(trans-cinnamoylamino)butoxy]benzamide; N-hydroxy-4-{2-[4-(2-methoxyethoxy)quinolin-2-ylcarbonylamino]ethoxy}benzamide; N-hydroxy-4-[2S-(benzothiophen-2-ylcarbonylamino)butoxy]benzamide; N-hydroxy-4-{2S-[benzofuran-2-ylcarbonylamino]butoxy}benzamide; N-hydroxy-4-{2-[3-(methoxymethyl)benzofuran-2-ylcarbonylamino]ethoxy}benzamide; N-hydroxy-4-{2-[3-(N,N-dimethylaminomethyl)benzofuran-2-ylcarbonylamino]ethoxy}-benzamide; N-hydroxy-4-{2-[3-(1-propoxymethyl)benzofuran-2-ylcarbonylamino]ethoxy}benzamide; N-hydroxy-4-{2-[3-(3-hydroxypropoxymethyl)benzofuran-2-ylcarbonylamino]ethoxy}-benzamide; N-hydroxy-4-{2-[3-(2-methoxyethyloxymethyl)benzofuran-2-ylcarbonylamino]ethoxy}-benzamide; N-hydroxy-4-{2-[3-(pyrrolidin-1-ylmethyl)benzofuran-2-ylcarbonylamino]ethoxy}-benzamide; N-hydroxy-4-{2-[3-(piperidin-1-ylmethyl)benzofuran-2-ylcarbonylamino]ethoxy}-benzamide; N-hydroxy-4-{2-[3-(4-methylpiperazin-1-ylmethyl)benzofuran-2-ylcarbonylamino]- ethoxy}benzamide; N-hydroxy-4-{2-[5-(tetrahydropyran-4-yloxy)benzofuran-2-ylcarbonylamino]ethoxy}-benzamide; N-hydroxy-4-{2-[5-(2-pyrrolidin-1-ylethyloxy)benzofuran-2-ylcarbonylamino]ethoxy}-benzamide; N-hydroxy-4-{2S-[5-(2-pyrrolidin-1-ylethyloxy)benzofuran-2-ylcarbonylamino]butoxy}-benzamide; N-hydroxy-4-{2-[5-(2-pyrrolidin-1-ylethyloxy)benzofuran-2-ylcarbonylamino]-1R-methyl-ethoxy}benzamide; N-hydroxy-4-{2-[(3-(benzofuran-2-yl)-4-(dimethylamino)-but-2-enoyl)amino]-ethoxy}benzamide; or a pharmaceutically acceptable salt thereof.

In some embodiments, the HDAC inhibitor is the HCl salt of N-hydroxy-4-{2-[3-(N,N-dimethylaminomethyl)benzofuran-2-ylcarbonylamino]ethoxy}-benzamide.

In some embodiments, the 5 to 9 consecutive days of daily administration of the pharmaceutical composition comprising the HCl salt of N-hydroxy-4-{2-[3-(N,N-dimethylaminomethyl)benzofuran-2-ylcarbonylamino]ethoxy}-benzamide comprises: daily administration of two immediate release pharmaceutical compositions comprising the HCl salt of Compound 1, wherein the two immediate release pharmaceutical compositions are administered 4 to 6 hours apart; or daily administration of a single controlled release oral solid dosage pharmaceutical composition.

In some embodiments, the 5 to 9 consecutive days of daily administration of the pharmaceutical composition comprising the HCl salt of N-hydroxy-4-{2-[3-(N,N-dimethylaminomethyl)benzofuran-2-ylcarbonylamino]ethoxy}-benzamide comprises daily administration of about 10 mg to about 300 mg of the HCl salt of N-hydroxy-4-{2-[3-(N,N-dimethylaminomethyl)benzofuran-2-ylcarbonylamino]ethoxy}-benzamide.

In some embodiments, the cancer is a hematological cancer, solid tumor or a sarcoma. In some embodiments, the cancer is breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinoma, gastrointestinal stromal tumor, pancreatic cancer, germ cell tumors, mast cell tumors, neuroblastoma, mastocytosis, testicular cancers, glioblastomas, astrocytomas, B cell lymphoma, T cell lymphoma, Hodgkin's lymphoma, non-Hodgkin's lymphoma, melanoma, myeloma, acute myelocytic leukemia (AML), acute lymphocytic leukemia (ALL), myelodysplastic syndrome, and chronic myelogenous leukemia.

In some embodiments, the method further comprises administering to the human at least one additional therapeutic agent selected from DNA-damaging agents; topoisomerase I or II inhibitors; alkylating agents; PARP inhibitors; proteasome inhibitors; RNA/DNA antimetabolites; antimitotics; immunomodulatory agents; antiangiogenics; aromatase inhibitors; hormone-modulating agents; apoptosis inducing agents; kinase inhibitors; monoclonal antibodies; abarelix; ABT-888; aldesleukin; aldesleukin; alemtuzumab; alitretinoin; allopurinol; altretamine; amifostine anastrozole; arsenic trioxide; asparaginase; azacitidine; AZD-2281; bendamustine; bevacizumab; bexarotene; bleomycin; bortezomib; BSI-201; busulfan; busulfan; calusterone; capecitabine; carboplatin; carfilozib; carmustine; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine; denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzamab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; meclorethamine; megestrol acetate; melphalan; mercaptopurine; methotrexate; methoxsalen; mitomycin C; mitomycin C; mitotane; mitoxantrone; nandrolone phenpropionate; nelarabine; NPI-0052; nofetumomab; oprelvekin; oxaliplatin; paclitaxel; paclitaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium; procarbazine; quinacrine; RAD001; rasburicase; rituximab; sargramostim; Sargramostim; sorafenib; streptozocin; sunitinib malate; tamoxifen; temozolomide; teniposide; testolactone; thalidomide; thioguanine; thiotepa; topotecan; toremifene; tositumomab; tositumomab/I-131 tositumomab; trastuzumab; tretinoin; uracil Mustard; valrubicin; vinblastine; vincristine; vinorelbine; vorinostat; zoledronate; and zoledronic acid.

In some embodiments, the method further comprises radiation therapy.

In one aspect, described herein is a method of treating cancer in a human comprising administering to the human a pharmaceutical composition comprising the HCl salt of N-hydroxy-4-{2-[3-(N,N-dimethylaminomethyl)benzofuran-2-ylcarbonylamino]ethoxy}-benzamide (Compound 1) and at least one pharmaceutically acceptable excipient in cycles consisting of 5 to 9 consecutive days of daily administration of the pharmaceutical composition comprising the HCl salt of Compound 1 followed by 5 to 7 consecutive days with no administration of the pharmaceutical composition comprising the HCl salt of Compound 1. In some embodiments, the 5 to 9 consecutive days of daily administration of the pharmaceutical composition comprising the HCl salt of Compound 1 comprises daily administration of two immediate release doses of a pharmaceutical composition comprising the HCl salt of Compound 1, wherein the two immediate release doses are administered 4 to 6 hours apart.

In some embodiments, the 5 to 9 consecutive days of daily administration of the pharmaceutical composition comprising the HCl salt of Compound 1 comprises administering a single controlled release oral solid dosage pharmaceutical composition as described herein.

In some embodiments, the 5 to 9 consecutive days of daily administration of the pharmaceutical composition comprising the HCl salt of Compound 1 comprises about 10 mg to about 300 mg of the HCl salt of Compound 1.

In one aspect, the method of treating cancer with a HDAC inhibitor as described herein decreases the incidence of grade 4 thrombocytopenia in the human with cancer.

In one aspect is the use of the HCl salt of Compound 1 in the manufacture of a controlled release pharmaceutical composition for oral administration to a human with cancer.

In one aspect is the use of a controlled release pharmaceutical composition of the HCl salt of Compound 1 for treating cancer in a human.

In one aspect is a dosing regimen of a pharmaceutical composition for use in the treatment of cancer in a human, wherein the pharmaceutical composition includes Compound 1, or a pharmaceutically acceptable salt thereof and the dosing regimen reduces the incidence of grade 4 thrombocytopenia in the human with cancer.

In one aspect, disclosed herein is a controlled release oral solid dosage pharmaceutical composition comprising Compound 1:

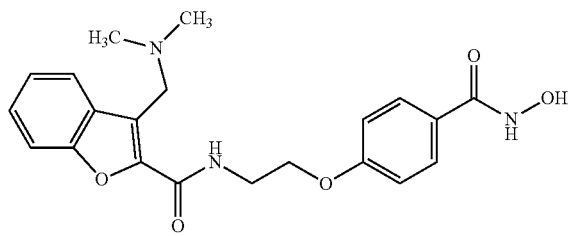

Compound 1 or a pharmaceutically acceptable salt thereof; and at least one pharmaceutically acceptable excipient, wherein the pharmaceutical composition completely releases Compound 1, or a pharmaceutically acceptable salt thereof, over a period of about 6 hours to about 10 hours after oral administration to a human.

In one aspect, Compound 1 is present in the pharmaceutical compositions as the HCl salt.

In some embodiments, the pharmaceutical composition completely releases Compound 1, HCl: (i) at a constant rate over a period of about 6 hours to about 10 hours after oral administration to a human; (ii) at a decreasing rate over a period of about 6 hours to about 10 hours after oral administration to a human; or (iii) in pulses over a period of about 6 hours to about 10 hours after oral administration to a human.

In some embodiments, the pharmaceutical composition completely releases Compound 1, HCl within 10 hours after oral administration to a human.

In some embodiments, the pharmaceutical composition releases less than about 10% of Compound 1, HCl in the stomach after oral administration to the human.

In some embodiments, the pharmaceutical composition does not release Compound 1, HCl in the stomach after oral administration to the human.

In some embodiments, the pharmaceutical composition comprises Compound 1, HCl in a controlled release matrix.

In some embodiments, the pharmaceutical composition is in the form of a tablet with an enteric coating.

In some embodiments, the enteric coating comprises: hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, cellulose ester-ether phthalate, hydroxypropylcellulose phthalate, alkali salts of cellulose acetate phthalate, alkaline earth salts of cellulose acetate phthalate, hydroxypropylmethyl cellulose phthalate, cellulose acetate phthalate, carboxymethylcellulose sodium, acrylic acid polymers and copolymers, ethyl acrylate/methyl methacrylate/ethyl trimethylammonium chloride methacrylate terpolymer, methacrylic acid/ethyl acrylate copolymer, methacrylic acid/methyl methacrylate copolymer, polyvinyl pyrrolidone, polyvinyl acetate, polyvinylacetate phthalate, vinylacetate crotonic acid copolymer; shellac, ammoniated shellac, shellac-acetyl alcohol, or shellac n-butyl stearate.

In some embodiments, the pharmaceutical composition comprises particles of Compound 1, HCl.

In some embodiments, the pharmaceutical composition completely releases Compound 1, HCl in pulses over a period of about 6 hours to about 10 hours.

In some embodiments, the pharmaceutical composition comprises at least two different groups of particles of Compound 1, HCl.

In some embodiments, the pharmaceutical composition comprises a first group of delayed release particles of Compound 1, HCl and a second groups of delayed release particles of Compound 1, HCl.

In some embodiments, the delayed particles of Compound 1, HCl are in the form of beads, pellets, granules, or minitablets.

In some embodiments, the first group of delayed release particles of Compound 1, HCl delays the release of Compound 1, HCl by at least 1-2 hours after oral administration to a human.

In some embodiments, the second group of delayed release particles of Compound 1, HCl delays the release of Compound 1, HCl by at least 3-6 hours after oral administration to a human.

In some embodiments, the release of Compound 1, HCl from the second group of delayed release particles occurs 2-6 hours following the release of at least half of the amount of Compound 1, HCl from the first group of delayed release particles after administration to a human.

In some embodiments, the pharmaceutical composition releases Compound 1, HCl in two pulses, where the second pulse of Compound 1, HCl occurs 2 to 6 hours after the first pulse of Compound 1, HCl after oral administration to the human.

In some embodiments, the amount of Compound 1, HCl is the same in the two groups of particles.

In some embodiments, the delayed release coating on the first group of delayed release particles is different from the delayed release coating on the second group of delayed release particles.

In some embodiments, the delayed release coatings comprise a pH sensitive coating or a pH insensitive coating.

In some embodiments, the pharmaceutical composition is in the form of pellets, beads, granules or minitablets in a capsule.

In some embodiments, the pharmaceutical composition is in the form of pellets, beads, or granules that are compressed into a single tablet.

In some embodiments, the pharmaceutical composition comprises about 10 mg to about 300 mg of Compound 1, HCl.

In some embodiments, the pharmaceutical composition provides a dose-normalized mean $AUC_{0-8h}$ from about 0.0035 to about 0.0124 $(\mu M \cdot h)/(mg/m^2)$ when orally administered to humans.

In one aspect, the pharmaceutical composition is for use in the treatment of cancer in a human. In some embodiments, the cancer is a hematological cancer, solid tumor or a sarcoma. In some embodiments, the cancer is breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinoma, gastrointestinal stromal tumor, pancreatic cancer, germ cell tumors, mast cell tumors, neuroblastoma, mastocytosis, testicular cancers, glioblastomas, astrocytomas, a lymphoma, melanoma, myeloma, acute myelocytic leukemia (AML), acute lymphocytic leukemia (ALL), myelodysplastic syndrome, and chronic myelogenous leukemia. In one aspect, the cancer is a lymphoma or a leukemia. In one aspect, the cancer is a B cell lymphoma, T cell lymphoma, Hodgkin's lymphoma, or non-Hodgkin's lymphoma. In one aspect, the cancer is non-Hodgkin's lymphoma.

In some embodiments, the pharmaceutical composition is used in combination with radiation therapy.

In some embodiments, the pharmaceutical composition is used in combination with at least one additional therapeutic agent selected from DNA-damaging agents; topoisomerase I or II inhibitors; alkylating agents; PARP inhibitors; proteasome inhibitors; RNA/DNA antimetabolites; antimitotics; immunomodulatory agents; antiangiogenics; aromatase inhibitors; hormone-modulating agents; apoptosis inducing agents; kinase inhibitors; monoclonal antibodies; abarelix; ABT-888; aldesleukin; aldesleukin; alemtuzumab; alitretinoin; allopurinol; altretamine; amifostine anastrozole; arsenic trioxide; asparaginase; azacitidine; AZD-2281; bendamustine; bevacizumab; bexarotene; bleomycin; bortezomib; BSI-201; busulfan; busulfan; calusterone; capecitabine; carboplatin; carfilozib; carmustine; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine; denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzamab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; meclorethamine; megestrol acetate; melphalan; mercaptopurine; methotrexate; methoxsalen; mitomycin C; mitomycin C; mitotane; mitoxantrone; nandrolone phenpropionate; nelarabine; NPI-0052; nofetumomab; oprelvekin; oxaliplatin; paclitaxel; paclitaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium; procarbazine; quinacrine; RAD001; rasburicase; rituximab; sargramostim; Sargramostim; sorafenib; streptozocin; sunitinib malate; tamoxifen; temozolomide; teniposide; testolactone; thalidomide; thioguanine; thiotepa; topotecan; toremifene; tositumomab; tositumomab/I-131 tositumomab; trastuzumab; tretinoin; uracil Mustard; valrubicin; vinblastine; vincristine; vinorelbine; vorinostat; zoledronate; and zoledronic acid.

Articles of manufacture, which include packaging material, a HDAC inhibitor compound described herein, which is effective for selectively inhibiting histone deacetylase activity, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for inhibiting the activity of histone deacetylase, or for the treatment, prevention or amelioration of one or more symptoms of a disease or condition that would benefit from inhibition of histone deacetylase activity, are provided.

In some embodiments, pharmaceutical compositions described herein that include a HDAC inhibitor are formulated in a manner that is suitable for oral administration to a human.

In some embodiments, pharmaceutical compositions described herein that include a HDAC inhibitor are formulated in a manner that is suitable for intravenous administration to a human.

Other objects, features and advantages of the methods, compounds, and compositions described herein will become apparent from the following detailed description. It should be understood, however, that the detailed description and the specific examples, while indicating specific embodiments, are given by way of illustration only, since various changes and modifications within the spirit and scope of the disclosure will become apparent to those skilled in the art from this detailed description.

DETAILED DESCRIPTION

Figure 1:
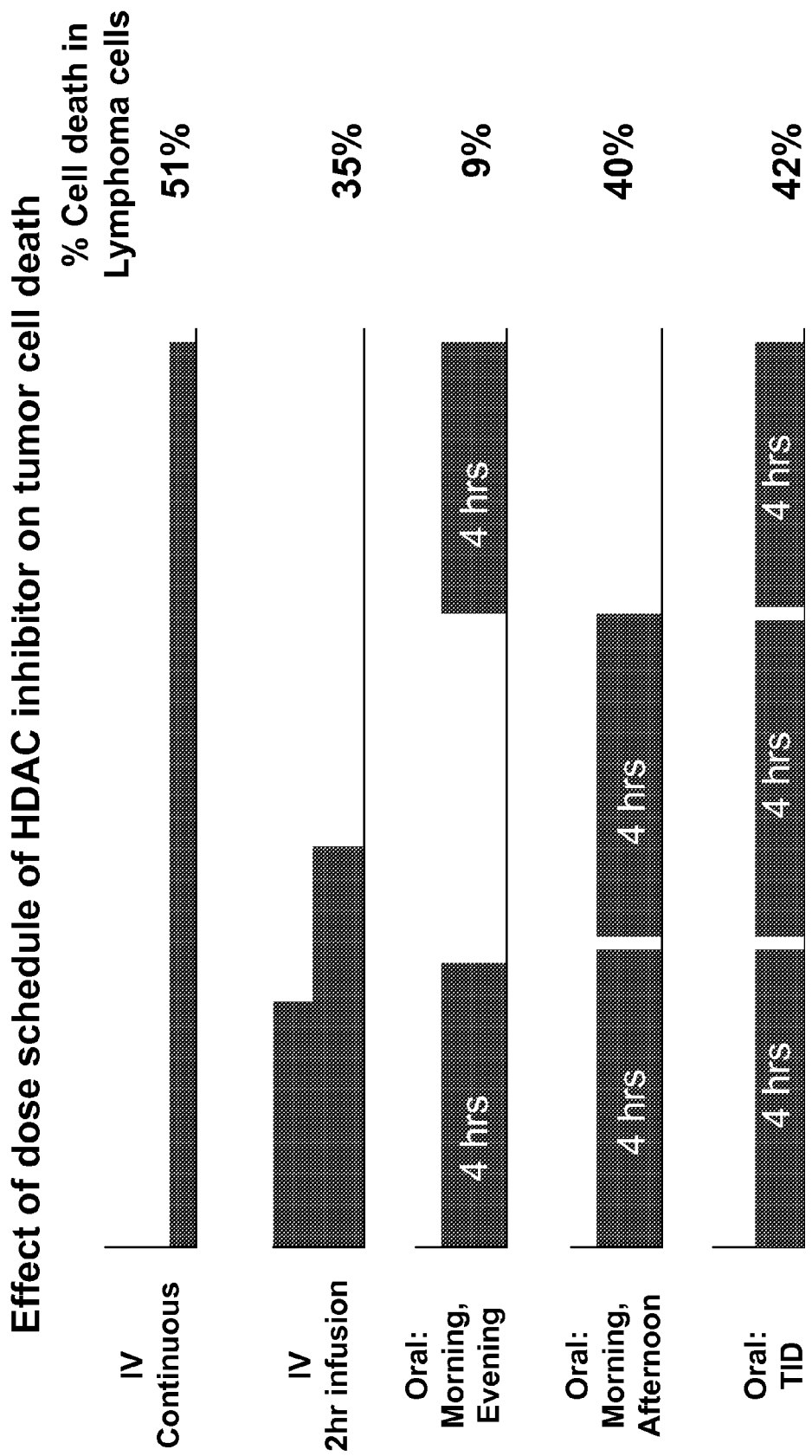
FIG. 1 presents the results of in vitro dose scheduling studies. The effect of dose schedule of HDAC inhibitor on tumor cell death is presented.

Cancer is considered a disease of genetic defects such as a gene mutations and deletions, as well as chromosomal abnormalities, that result in the loss of function of tumor suppressor genes and/or gain of function or hyperactivation of oncogenes.

Cancer is characterized by genome-wide changes in gene expression within the tumor. These changes favor a tumor's ability to progress through the cell cycle, to avoid apoptosis, or to become resistant to chemotherapy. HDAC inhibitors are able to reverse several of these changes, and restore a pattern more like that of a normal cell.

The human genome consists of a complex network of genes which are turned on or off depending on the needs of the cell. One of the ways in which genes are turned on or off is by means of chemical modification of histone proteins. Histone proteins are structural components of chromosomes, and form a scaffold upon which DNA, the genetic material, is arranged. A well studied histone modification is acetylation and deacetylation, modifications that are catalyzed by a family of enzymes known as histone acetyl transferases and histone deacetylases.

Inhibition of HDAC enzymes by Compound 1 tips the balance in favor of the acetylated state, a state that allows transcription to occur, which can be thought of as turning a gene "on". When a cell is treated with Compound 1, waves of previously silenced genes are initially turned on. Some of these genes are regulators themselves, and will activate or repress the expression of still other genes. The result is an orchestra of changes to gene expression: some genes being turned on, while others are kept in the off state.

Following chemotherapy and/or radiation treatment, some patient's tumors may turn on certain genes as a strategy by the tumor to adapt to the therapy and become resistant to cell death. One example of a genetic change that occurs in many cancers is the activation of the DNA repair gene RAD51. In response to treatment with DNA-damaging chemotherapy or radiation, tumors will often turn on DNA repair genes (including RAD51) as an adaptive strategy to help the tumor repair the DNA damage done by these agents. In pre-clinical models, Compound 1 was able to turn off RAD51 (and other DNA repair genes), effectively blocking the ability of the tumor to repair its damaged DNA, sensitizing the tumor to chemotherapy and radiation.

HDAC Inhibitor Preclinical Activities

In preclinical studies Compound 1 has been found to have anticancer activities with remarkable tumor specificity. These early studies provided important information about the in vitro and in vivo activities of Compound 1 and determined the molecular mechanism underlying the anticancer effects.

In vitro: Compound 1 is active against many tumor cell lines and is efficacious in mouse models of lung, colon, prostate, pancreatic and brain tumors.

Ex vivo: Compound 1 is active in primary human tumors from patients with colon, ovarian, lung and many hematological cancers.

Extensive safety and toxicology studies have been completed in multiple animal species. The mechanism of action of Compound 1 has been studied, and involves a multi-pronged attack on tumor cells: upregulation of p21 and other tumor suppressors and cell cycle genes; induction of reactive oxygen species and attenuation of anti-oxidant pathways; alterations in calcium homeostasis and increased ER stress; downregulation of DNA repair pathways and increased DNA damage; direct induction of apoptosis via death receptors and activation of caspases.

Compound 1 is a hydroxamate-based HDAC inhibitor. Described herein are pharmaceutical compositions that include Compound 1, as well as pharmacokinetic and pharmacodynamic strategies, dosing regimens, as well as methods of treating cancers in a human, either as monotherapy or combination therapy.

Therapeutic and Pharmacodynamic Effect to Compound 1

In clinical trials involving humans with cancer, Compound 1 in solution form was administered at 2 mg/kg as a single oral dose and as multiple 2-hour IV infusion doses. Systemic exposure measured as $AUC_{0-\infty}$ for IV and oral dosing was 5.9 µM*hr and 1.45 µM*hr, respectively, indicating an oral bioavailability of about 27% in humans.

A therapeutic effect of an HDAC inhibitor (e.g. Compound 1) is achieved in humans with cancer by administering the HDAC inhibitor orally twice a day (with the two doses being administered consecutively about 4 to about 6 hours apart), orally three time a day (with the doses being administered consecutively about 4 to about 6 hours apart), intravenously, or continuously. The aforementioned dosing regimens facilitate the ability to maintain in the human at least 6 consecutive hours of effective plasma concentrations of the HDAC inhibitor.

A therapeutic effect of Compound 1 is achieved in humans with cancer by administering Compound 1 (immediate release oral capsules) twice a day, with the two doses being administered about 4 to about 6 hours apart. In some embodiments, twice a day dosing reduces the incidences of thrombocytopenia as compared to three times a day dosing.

For therapeutic effect, effective plasma concentrations of Compound 1 in humans should be maintained for at least 6 consecutive hours, at least 7 consecutive hours, or at least 8 consecutive hours each day on days of dosing. For therapeutic effect, effective plasma concentrations of Compound 1 in humans should be maintained for at least 6 consecutive hours each day on days of dosing. For therapeutic effect, effective plasma concentrations of Compound 1 in humans should be maintained for at least 7 consecutive hours each day on days of dosing. In some embodiments, for therapeutic effect, effective plasma concentrations of Compound 1 in humans should be maintained for about 6 consecutive hours to about 8 consecutive hours each day on days of dosing. In some embodiments, effective plasma concentrations of Compound 1 in humans are maintained for at least 6 consecutive hours but not exceeding 12, 13, or 14 consecutive hours on days of dosing. In some embodiments, maintaining the effective plasma concentrations for at least 6 consecutive hours but not exceeding 14 consecutive hours of Compound 1 on days of dosing increases the efficacy of tumor cell growth inhibition and minimizes the incidences of thrombocytopenia. In some embodiments, maintaining the effective plasma concentrations for about 6 consecutive hours to about 8 consecutive hours of Compound 1 on days of dosing increases the efficacy of tumor cell growth inhibition and minimizes the incidences of thrombocytopenia.

The oral bioavailability of Compound 1 in humans, administered as immediate release capsules or an oral solution, was determined to be about 27%. A difference in pharmacokinetics was observed in laboratory animals between the fasted state the fed state. Compound 1 appears to be preferentially absorbed in the intestines.

In one aspect, presented herein are methods of providing reliable for therapeutic and pharmacodynamic effect to Compound 1, or a pharmaceutically acceptable salt thereof, that include administering Compound 1, or a pharmaceutically acceptable salt thereof, in the form of a controlled release formulation. Controlled release formulations allow for once a day dosing. Controlled release formulations also allow for the release of the active agent (i.e. Compound 1, or a pharmaceutically acceptable salt thereof) in the intestines rather than in the stomach.

In one aspect, the controlled release formulation is a multi-particulate drug delivery system. Multi-particulate drug delivery systems are oral dosage forms consisting of a multiplicity of small discrete units, each exhibiting some desired characteristics. In these systems, the dosage of the drug substances is divided on a plurality of subunits, typically consisting of thousands of spherical particles with diameter of 0.05-2.00 mm. Multiparticulate dosage forms are pharmaceutical formulations in which the active substance is present as a number of small independent subunits. To deliver the recommended total dose, these subunits are filled into a capsule or compressed into a tablet. Multiparticulates are less dependent on gastric emptying, resulting in less inter and intra-subject variability in gastrointestinal transit time. They are also better distributed and less likely to cause local irritation or be influenced by the presence of food.

Multiparticulate dosage forms offer benefits such as increased bioavailability, reduced risk of local irritation and predictable gastric emptying. In some embodiments, multiparticulate systems show better reproducible pharmacokinetic behavior than conventional formulations.

After disintegration of a controlled release formulation (e.g. tablet or capsule) which occurs within a few minutes, the individual subunit particles pass rapidly through the GI tract. If these subunits have diameters of less than 2 mm, they are able to leave the stomach continuously, even if the pylorus is closed. These results in lower intra and inter individual variability in plasma levels and bioavailability.

Other controlled release oral pharmaceutical dosage forms are able to provide the same benefits that are observed with a multi-particulate drug delivery system.

Drug Holiday

Thrombocytopenia is a side effect observed in humans that receive treatment with a HDAC inhibitor compound. Thrombocytopenia is a condition in which there is a lower-than-normal number of platelets in the blood. It may result in easy bruising and excessive bleeding from wounds or bleeding in mucous membranes and other tissues. Thrombocytopenia has typically been reconciled by lowering the daily dose of the HDAC inhibitor compound that is administered to the human. However, a lowering of the daily dose of the HDAC inhibitor compound may not allow for therapeutic and for therapeutic and pharmacodynamic effect to the HDAC inhibitor compound.

Presented herein are dosing regimens for achieving for therapeutic and pharmacodynamic effect to an HDAC inhibitor with a limited incidence of Grade 4 thrombocytopenia that include 5-9 consecutive days of daily dosing of an HDAC inhibitor in an amount sufficient to maintain effective plasma concentrations of the HDAC inhibitor for at least 6 consecutive hours on each day of dosing, followed by 5-9 consecutive days without dosing the HDAC inhibitor. In some embodiments, on the days of dosing the effective plasma concentrations of the HDAC inhibitor are maintained for at least 6, at least 7, or at least 8 consecutive hours but not exceeding 12, 13, or 14 consecutive hours. In some embodiments, on the days of dosing the HDAC inhibitor is administered in an amount sufficient to maintain effective plasma concentrations of the HDAC inhibitor for about 6 consecutive hours to about 8 consecutive hours. In some embodiments, the HDAC inhibitor is administered orally. In some embodiments, on the days of dosing the effective plasma concentrations of the HDAC inhibitor are maintained for no more than 12, 13, or 14 consecutive hours. In other embodiments, the HDAC inhibitor is administered parenterally.

Presented herein are dosing regimens for achieving for therapeutic and pharmacodynamic effect to an HDAC inhibitor with a limited incidence of Grade 4 thrombocytopenia that include: (a) twice a day oral dosing of an HDAC inhibitor (immediate release oral pharmaceutical composition) for 7 consecutive days followed by 7 consecutive days without dosing the HDAC inhibitor; or (b) once a day dosing of an HDAC inhibitor (controlled release oral pharmaceutical composition) for 7 consecutive days followed by 7 consecutive days without dosing the HDAC inhibitor. The foregoing dosing regimen also includes 5-9 consecutive days of dosing with an HDAC inhibitor, followed by 2-9 days consecutive days of no dosing with an HDAC inhibitor.

Presented herein are dosing regimens for achieving for therapeutic and pharmacodynamic effect to Compound 1 with a limited incidence of Grade 4 thrombocytopenia that include: (a) twice a day oral dosing of Compound 1 (immediate release oral pharmaceutical composition) for 7 consecutive days followed by 7 consecutive days without dosing Compound 1; (b) once a day dosing of Compound 1 (controlled release oral pharmaceutical composition) for 7 consecutive days followed by 7 consecutive days without dosing Compound 1. The foregoing dosing regimen also includes 5-9 consecutive days of dosing with Compound 1, followed by 2-9 days consecutive days of no dosing with Compound 1.

The foregoing dosing regimen also includes 5-9 consecutive days of dosing with Compound 1, followed by 2-9 days consecutive days of no dosing with Compound 1.

HDAC Inhibitor Compounds

N-hydroxy-4-{2-[3-(N,N-dimethylaminomethyl)benzofuran-2-ylcarbonylamino]ethoxy}-benzamide (Compound 1) has the following structure:

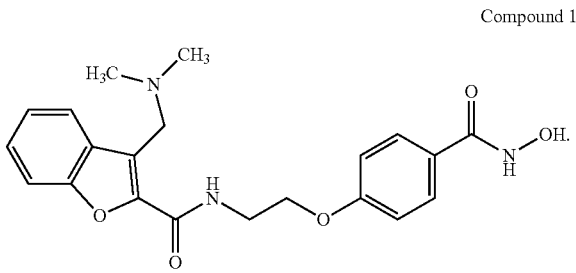 [SMILES: CN(C)Cc1c(C(=O)NCCOc2ccc(C(=O)NO)cc2)oc2ccccc12]

Compound 1

In one aspect, Compound 1 is used in the pharmaceutical compositions and methods disclosed herein as a pharmaceutically acceptable salt. In one aspect, Compound 1 is used as the hydrochloride salt.

Additional pharmaceutically acceptable salts of Compound 1 include: (a) salts formed when the acidic proton of Compound 1 is replaced by a metal ion, such as for example, an alkali metal ion (e.g. lithium, sodium, potassium), an alkaline earth metal ion (e.g. magnesium, or calcium), or an aluminum ion, or is replaced by an ammonium cation ($NH_4^+$); (b) salts formed by reacting Compound 1 with a pharmaceutically acceptable organic base, which includes alkylamines, such as ethanolamine, diethanolamine, triethanolamine, tromethamine, N-methylglucamine, dicyclohexylamine, tris (hydroxymethyl)methylamine, and salts with amino acids such as arginine, lysine, and the like; (c) salts formed by reacting Compound 1 with a pharmaceutically acceptable acid, which provides acid addition salts. Pharmaceutically acceptable acids include hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Additional pharmaceutically acceptable salts include those described in Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002.

In some embodiments, sites on the aromatic ring portion of compounds described herein that are susceptible to various metabolic reactions are modified such that the various metabolic reactions are reduced, minimized or eliminated. Such modifications include incorporation of appropriate substituents on the aromatic ring structures, such as, by way of example only, halogens, deuterium, and the like. In one aspect, HDAC inhibitor compounds described herein are deuterated at sites susceptible to metabolic reactions.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

Other HDAC inhibitor compounds that are contemplated for use in the pharmaceutical compositions, pharmacokinetic strategies, dosing regimens, methods of treatments, and combination therapies include those compounds with the structure of Formula (I):

Formula (I)

[Chemical structure of Formula (I): Ar-C(=O)-N(R³)-Y-X-[benzene ring]-C(=O)-NH-OH]

wherein:
X is —O—, —NR²—, or —S(O)$_n$— where n is 0, 1, or 2 and R² is hydrogen, —CH$_3$, —CH$_2$CH$_3$;
Y is ethylene, propylene, 1-methylpropylene, 2-methylpropylene, —CH(C$_2$H$_5$)CH$_2$—, —CH(CH(CH$_3$)$_2$)CH$_2$—, and —CH(CH$_3$)CH$_2$—;
R³ is hydrogen, —CH$_3$, or —CH$_2$CH$_3$;
Ar is phenyl, naphthyl, quinolinyl, benzofuranyl, benzothienyl, trans phenylCH═CH— or trans (benzofuran-2-yl)CH═CH—, wherein Ar is optionally substituted with one or two substituents independently selected from chloro, fluoro, trifluoromethyl, methyl, ethyl, methoxy, ethoxy, methylenedioxy, —OH, 1-cyclopropylpiperidin-4-yloxy, 1-(2,2,2-trifluoroethyl)piperidin-4-yloxy, N,N-dimethylaminomethyl, N,N-diethylaminomethyl, 2-methoxyethoxymethyl, phenoxymethyl, 2-methoxyethoxy, 2-morpholin-4-ylethoxy, pyridin-3-ylmethoxy, 2-hydroxyethoxy, 2-N,N-dimethylaminoethoxy, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 4-[1.2.4-triazin-1-yl-phenoxymethyl, 2-phenylethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, pyridin-3-ylmethyloxymethyl, tetrahydropyran-4-yloxy, 2,2,2-trifluoroethyloxy, 2-pyrrolidin-1-ylethyloxy, piperidin-4-yloxy, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonyl-methylaminomethyl, or 3-(2-carboxyethylaminomethyl); or
a pharmaceutically acceptable salt thereof.

In some embodiments, Ar is benzofuran-2-yl and is mono-substituted at the 3-position of the benzofuran-2-yl ring with N,N-dimethylaminomethyl, N,N-diethylaminomethyl, 2-fluorophenoxymethyl, 3-fluorophenoxymethyl, 4-fluorophenoxy-methyl, hydroxyl-4-yloxymethyl, 2,4,6-trifluorophenoxy-methyl, 2-oxopyridin-1-ylmethyl, 2,2,2-trifluoroethoxy-methyl, 4-imidazol-1-ylphenoxy-methyl, 4-[1.2.4-triazin-1-yl-phenoxymethyl, 2-phenylethyl, 3-hydroxypropyloxymethyl, 2-methoxyethyloxymethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonylmethyl, 2-(3-trifluoromethoxyphenylethyl), N-methyl-N-benzylaminomethyl, N-methyl-N-2-phenylethylaminomethyl, 3-hydroxypropyl-thiomethyl, 3-hydroxypropylsulfinyl-methyl, 3-hydroxypropylsulfonylmethyl, N-methyl-N-2-indol-3-ylethylaminomethyl, 2-(4-trifluoromethylphenyl)ethyl, N-hydroxyaminocarbonyl-methylaminomethyl, or 2-carboxyethylaminomethyl.

In some embodiments, Ar is benzofuran-2-yl and is mono-substituted at the 3-position of the benzofuran-2-yl ring with N,N-dimethylaminomethyl, N,N-diethylaminomethyl, 2-methoxyethoxymethyl, methoxymethyl, 3-i-propoxymethyl, morpholin-4-ylmethyl, 3-hydroxypropyloxymethyl, 3-methoxypropyloxymethyl, pyrrolidin-1-ylmethyl, or piperidin-1-ylmethyl.

In some embodiments, Ar is benzofuran-2-yl and is substituted at the 5-position of the benzofuran-2-yl ring with 1-cyclopropylpiperidin-4-yloxy, piperidin-4-yloxy, tetrahydropyran-4-yloxy, 2,2,2-trifluoroethoxy, 2-pyrrolidin-1-ylethyloxy, or 1-(2,2,2-trifluoroethyl)piperidin-4-yloxy.

In some embodiments, Ar is trans phenylCH═CH— wherein the phenyl is optionally substituted with one or two substituents independently selected from methyl, ethyl, methoxy, ethoxy, methylenedioxy, or —OH. In some embodiments, Ar is trans phenylCH═CH—.

In some embodiments, Ar is naphthyl wherein the naphthyl is optionally substituted with one or two substituents.

In some embodiments, Ar is quinolinyl wherein the quinolinyl is optionally substituted with one or two substituents.

In some embodiments, Ar is quinolinyl wherein the quinolinyl is optionally substituted with one or two substituents independently selected from chloro, fluoro, trifluoromethyl, methyl, ethyl, methoxy, ethoxy, methylenedioxy, —OH, 2-methoxyethoxy, 2-hydroxyethoxy, methoxymethyl, 3-i-propoxymethyl, 3-hydroxypropyloxymethyl, 3-methoxypropyloxymethyl, or 3,3,3-trifluoropropyloxymethyl.

In some embodiments, X is —O— and R³ is hydrogen.
In some embodiments, X is —S(O)$_n$— and R³ is hydrogen.
In some embodiments, Y is ethylene. In some embodiments, Y is ethylene or —CH(C$_2$H$_5$)CH$_2$—. In some embodiments, Y is —CH(C$_2$H$_5$)CH$_2$—.
In some embodiments, X is —O—; R³ is hydrogen; and Y is ethylene or —CH(C$_2$H$_5$)CH$_2$—.

Yet other HDAC inhibitor compounds that are contemplated for use in the pharmaceutical compositions, pharmacokinetic strategies, dosing regimens, methods of treatments, and combination therapies include those compounds with the structure of Formula (II):

Formula (II)

[Chemical structure of Formula (II): Ar-C(R⁵)=CH-C(=O)-N(R³)-Y-O-[benzene ring]-C(=O)-NH-OH]

wherein:
X is —O—, —NR²—, or —S(O)$_n$— where n is 0, 1, or 2 and R² is hydrogen, —CH$_3$, —CH$_2$CH$_3$;
Y is ethylene, propylene, 1-methylpropylene, 2-methylpropylene, —CH(C$_2$H$_5$)CH$_2$—, —CH(CH(CH$_3$)$_2$)CH$_2$—, and —CH(CH$_3$)CH$_2$—;
R³ is hydrogen, —CH$_3$, or —CH$_2$CH$_3$;

Ar is phenyl, naphthyl, quinolinyl, benzofuranyl, or benzothienyl, wherein Ar is optionally substituted with one or two substituents independently selected from chloro, fluoro, trifluoromethyl, methyl, ethyl, methoxy, ethoxy, methylenedioxy, —OH;

$R^5$ is trifluoromethyl, methyl, ethyl, N,N-dimethylaminomethyl, N,N-diethylaminomethyl, 2-methoxyethoxymethyl, phenoxymethyl, methoxymethyl, 3-i-propoxymethyl, morpholin-4-ylmethyl, 3-hydroxypropyloxymethyl, 2-fluorophenoxymethyl, 3-fluorophenoxymethyl, 4-fluorophenoxy-methyl, 3-methoxypropyloxymethyl, pyridin-4-yloxymethyl, 2,4,6-trifluorophenoxymethyl, 2-oxopyridin-1-ylmethyl, 2,2,2-trifluoroethoxymethyl, 4-imidazol-1-ylphenoxymethyl, 2-phenylethyl, pyrrolidin-1-ylmethyl, piperidin-1-ylmethyl, 4-trifluoromethylpiperidin-1-ylmethyl, 4-methylpiperazin-1-ylmethyl, 3,3,3-trifluoropropyloxymethyl, 4-fluorophenylthiomethyl, 4-fluorophenylsulfinylmethyl, 4-fluorophenylsulfonyl-methyl, pyridin-3-ylmethyloxymethyl, N-methyl-N-benzylaminomethyl, N-methyl-N-2-phenylethylaminomethyl, 3-hydroxypropylthiomethyl, 3-hydroxypropylsulfinylmethyl, 3-hydroxypropylsulfonyl-methyl, N-methyl-N-2-indol-3-ylethylaminomethyl, 2-(4-trifluoromethylphenyl)ethyl, 2-(3-trifluoromethoxyphenyl)ethyl, N-hydroxyaminocarbonylmethylaminomethyl, or 3-(2-carboxyethylaminomethyl); or a pharmaceutically acceptable salt thereof.

In some embodiments, Ar is benzofuranyl.

In some embodiments, $R^5$ is N,N-dimethylaminomethyl, N,N-diethylaminomethyl, pyrrolidin-1-ylmethyl, or piperidin-1-ylmethyl.

In some embodiments, the HDAC inhibitor is selected from: N-hydroxy-4-[2-(4-methoxyquinolin-2-ylcarbonylamino)ethoxy]benzamide; N-hydroxy-4-[2S-(trans-cinnamoylamino)butoxy]benzamide; N-hydroxy-4-[2R-(trans-cinnamoylamino)butoxy]benzamide; N-hydroxy-4-{2-[4-(2-methoxyethoxy)quinolin-2-ylcarbonylamino]ethoxy}benzamide; N-hydroxy-4-[2S-(benzothiophen-2-ylcarbonylamino)butoxy]-benzamide; N-hydroxy-4-{2S-[benzofuran-2-ylcarbonylamino]butoxy}benzamide; N-hydroxy-4-{2-[3-(methoxymethyl)benzofuran-2-ylcarbonylamino]ethoxy}benzamide; N-hydroxy-4-{2-[3-(N,N-dimethylaminomethyl)benzofuran-2-ylcarbonylamino]ethoxy}benzamide; N-hydroxy-4-{2-[3-(i-propoxymethyl)benzofuran-2-ylcarbonylamino]ethoxy}benzamide; N-hydroxy-4-{2-[3-(3-hydroxypropoxymethyl)benzofuran-2-ylcarbonylamino]ethoxy}-benzamide; N-hydroxy-4-{2-[3-(2-methoxyethyloxymethyl)benzofuran-2-ylcarbonylamino]ethoxy}-benzamide; N-hydroxy-4-{2-[3-(pyrrolidin-1-ylmethyl)benzofuran-2-ylcarbonylamino]ethoxy}-benzamide; N-hydroxy-4-{2-[3-(piperidin-1-ylmethyl)benzofuran-2-ylcarbonylamino]ethoxy}-benzamide; N-hydroxy-4-{2-[3-(4-methylpiperazin-1-ylmethyl)benzofuran-2-ylcarbonylamino]-ethoxy}benzamide; N-hydroxy-4-{2-[5-(tetrahydropyran-4-yloxy)benzofuran-2-ylcarbonylamino]ethoxy}-benzamide; N-hydroxy-4-{2-[5-(2-pyrrolidin-1-ylethyloxy)benzofuran-2-ylcarbonylamino]ethoxy}-benzamide; N-hydroxy-4-{2S-[5-(2-pyrrolidin-1-ylethyloxy)benzofuran-2-ylcarbonylamino]butoxy}-benzamide; N-hydroxy-4-{2-[5-(2-pyrrolidin-1-ylethyloxy)benzofuran-2-ylcarbonylamino]-1R-methyl-ethoxy}benzamide; and N-hydroxy-4-{2-[(3-(benzofuran-2-yl)-4-(dimethylamino)-but-2-enoyl)amino]-ethoxy}benzamide; or a pharmaceutically acceptable salt thereof.

In some embodiments, the HDAC inhibitor is selected from HDAC inhibitors disclosed in WO 2004/092115 or WO 2005/097770, both of which are herein incorporated by reference.

Forms and Phases

HDAC inhibitors (e.g. Compound 1), including pharmaceutically acceptable salts thereof, and pharmaceutically acceptable solvates thereof, are in various forms, including but not limited to, amorphous phase, partially crystalline forms, crystalline forms, milled forms, and nano-particulate forms. The crystalline forms are known as polymorphs. Polymorphs include the different crystal packing arrangements of the same elemental composition of a compound. This arrangement can significantly affect the physiochemical, formulation and processing parameters as well as the shelf life or stability of the substance and excipients. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature cause a single crystal form to dominate. In one aspect, a crystalline form of an HDAC inhibitor (e.g. Compound 1) is used in the pharmaceutical compositions disclosed herein. In one aspect, a crystalline form of the HCl salt of Compound 1 is used in the pharmaceutical compositions disclosed herein. In one aspect, amorphous Compound 1 is used in the pharmaceutical compositions disclosed herein. In one aspect, amorphous HCl salt of Compound 1 is used in the pharmaceutical composition disclosed herein.

Terminology

"Bioavailability" refers to the percentage of the weight of an HDAC inhibitor (e.g. Compound I), or a pharmaceutically acceptable salt, dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which an HDAC inhibitor (e.g. Compound 1), or a pharmaceutically acceptable salt, is absorbed into the general circulation when the pharmaceutical composition is taken orally as compared to intravenous injection.

"Blood plasma concentration" refers to the concentration an HDAC inhibitor (e.g. Compound I), or a pharmaceutically acceptable salt, in the plasma component of blood of a subject. It is understood that the plasma concentration of an HDAC inhibitor (e.g. Compound 1), or a pharmaceutically acceptable salt, may vary significantly between subjects, due to variability with respect to metabolism and/or interactions with other therapeutic agents. In one aspect, the blood plasma concentration of an HDAC inhibitor (e.g. Compound 1), or a pharmaceutically acceptable salt, varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of an HDAC inhibitor (e.g. Compound 1), or a pharmaceutically acceptable salt, varies from subject to subject.

"Effective plasma concentrations" of an HDAC inhibitor refers to amounts of the HDAC inhibitor in the plasma that result in exposure levels that are effective for treating a cancer.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

A "measurable serum concentration" or "measurable plasma concentration" describes the blood serum or blood plasma concentration, typically measured in mg, µg, or ng of therapeutic agent per ml, dl, or 1 of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

Pharmaceutical Compositions

In one embodiment, oral pharmaceutical compositions are formulated in a conventional manner using one or more physiologically acceptable carriers (i.e. inactive ingredients) comprising excipients and auxiliaries which facilitate processing of the active compounds into preparations which are used pharmaceutically. Suitable techniques, carriers, and excipients include those found within, for example, Remington: *The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

The term "pharmaceutical composition" refers to a mixture of an active agent (or ingredient) with other inactive chemical components, such as carriers, stabilizers, diluents, dispersing agents, suspending agents, thickening agents, coatings and/or excipients. The pharmaceutical composition facilitates administration of the compound to a human. In one aspect, the active agent is an HDAC inhibitor (e.g. Compound 1). In one aspect, the active agent is the HCl salt of Compound 1.

"Controlled release" as used herein refers to any release profile that is not entirely immediate release.

For oral administration, an HDAC inhibitor (e.g. Compound 1), or a pharmaceutically acceptable salt thereof, such as the HCl salt, are formulated by combining the active compound with pharmaceutically acceptable carriers or excipients. Such carriers enable an HDAC inhibitor (e.g. Compound 1), or a pharmaceutically acceptable salt thereof, to be formulated as tablets, powders, pills, capsules, and the like, for oral ingestion by a patient to be treated.

The pharmaceutical compositions will include at least one pharmaceutically acceptable carrier, diluent or excipient and an HDAC inhibitor (e.g. Compound 1), or a pharmaceutically acceptable salt thereof, as the active ingredient.

The oral solid dosage formulations described herein include particles of an HDAC inhibitor (e.g. Compound 1), or a pharmaceutically acceptable salt thereof, existing in crystalline form, amorphous phase, semi-crystalline form, semi-amorphous phase, or mixtures thereof.

In one aspect, pharmaceutical compositions disclosed herein are in the form of an oral solid dosage form. Oral solid dosage forms include: tablets, pills, capsule, powders, mini-tablets, particles, beads, pellets, and the like.

The pharmaceutical compositions described herein include an HDAC inhibitor (e.g. Compound I), or a pharmaceutically acceptable salt thereof, and one or more of the following: (a) binders; (b) coatings; (c) disintegrants; (d) fillers (diluents); (e) lubricants; (f) glidants (flow enhancers); (g) compression aids; (h) colors; (i) sweeteners; (j) preservatives; (k) suspensing/dispersing agents; (l) film formers/coatings; (m) flavors; (n) printing inks; (o) gelling agents; (p) a second therapeutically active agent.

In one aspect, pharmaceutical compositions described herein include one or more of the following in addition to the HDAC inhibitor (e.g. Compound 1), or a pharmaceutically acceptable salt thereof: (a) magnesium stearate; (b) lactose; (c) microcrystalline Cellulose; (d) silicified microcrystalline cellulose; (e) mannitol; (f) starch (corn); (g) silicon dioxide; (h) titanium dioxide; (i) stearic acid; (j) s Starch glycolate; (k) gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate.

Also provided herein are pharmaceutical compositions comprising an active ingredient, or a pharmaceutically acceptable salt, solvate, or prodrug thereof, in a pharmaceutically acceptable vehicle, carrier, diluent, or excipient, or a mixture thereof; and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. The pharmaceutical compositions may also comprise non-release controlling excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating. Granulation methods are described, for example, in Voigt, pages 156-69.

Suitable excipients for the production of granules are, for example pulverulent fillers optionally having flow-conditioning properties, for example talcum, silicon dioxide, for example synthetic amorphous anhydrous silicic acid of the Syloid® type (Grace), for example SYLOID 244 FP, microcrystalline cellulose, for example of the Avicel® type (FMC Corp.), for example of the types AVICEL PH101, 102, 105, RC581 or RC 591, Emcocel® type (Mendell Corp.) or Elcema® type (Degussa); carbohydrates, such as sugars, sugar alcohols, starches or starch derivatives, for example lactose, dextrose, saccharose, glucose, sorbitol, mannitol, xylitol, potato starch, maize starch, rice starch, wheat starch or amylopectin, tricalcium phosphate, calcium hydrogen phosphate or magnesium trisilicate; binders, such as gelatin, tragacanth, agar, alginic acid, cellulose ethers, for example methylcellulose, carboxymethylcellulose or hydroxypropylmethylcellulose, polyethylene glycols or ethylene oxide homopolymers, especially having a degree of polymerization of approximately from $2.0 \times 10^3$ to $1.0 \times 10^5$ and an approximate molecular weight of about from $1.0 \times 10^5$ to $5.0 \times 10^6$, for example excipients known by the name Polyox® (Union Carbide), polyvinylpyrrolidone or povidones, especially having a mean molecular weight of approximately 1000 and a degree of polymerization of approximately from about 500 to about 2500, and also agar or gelatin; surface-active substances, for example anionic surfactants of the alkyl sulfate type, for example sodium, potassium or magnesium n-dodecyl sulfate, n-tetradecyl sulfate, n-hexadecyl sulfate or n-octadecyl sulfate, of the alkyl ether sulfate type, for example sodium, potassium or magnesium n-dodecyloxyethyl sulfate, n-tetradecyloxyethyl sulfate, n-hexadecyloxyethyl sulfate or n-octadecyloxyethyl sulfate, or of the alkanesulfonate type, for example sodium, potassium or magnesium n-dodecanesulfonate, n-tetradecanesulfonate, n-hexadecanesulfonate or n-octadecanesulfonate, or non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol 400 stearate, polyethylene glycol 2000 stearate, especially ethylene oxide/propylene oxide block polymers of the Pluronics® (BWC) or Synperonic® (ICI) type Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions may also comprise non-release controlling excipients.

Additionally provided are pharmaceutical compositions in a dosage form that has an instant releasing component and at least one delayed releasing component, and is capable of giving a discontinuous release of the compound in the form of at least two consecutive pulses separated in time from 0.5 hour up to 8 hours. The pharmaceutical compositions comprise a combination of an active ingredient, and one or more release controlling and non-release controlling excipients, such as those excipients suitable for a disruptable semi-permeable membrane and as swellable substances.

Provided herein also are pharmaceutical compositions in a dosage form for oral administration to a subject, which comprises a combination of an active ingredient, or a pharmaceutically acceptable salt, solvate, or prodrug thereof; and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Provided herein are pharmaceutical compositions that comprise an active ingredient, in the form of enteric-coated granules, as delayed-release capsules for oral administration.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets or capsules.

Pharmaceutical dosage forms can be formulated in a variety of methods and can provide a variety of drug release profiles, including immediate release, sustained release, and delayed release. In some cases it may be desirable to prevent drug release after drug administration until a certain amount of time has passed (i.e. timed release), to provide substantially continuous release over a predetermined time period (i.e. sustained release) or to provide release immediately following drug administration (i.e., immediate release).

Oral formulations that include an HDAC inhibitor (e.g. Compound 1), or a pharmaceutically acceptable salt thereof, are presented in the form of: tablets, capsules, pills, pellets, beads, granules, bulk powders. Capsules include mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Tablet formulations are made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

In one aspect, oral formulations described herein utilize standard delay or time release formulations to alter the absorption of the active compound(s).

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL®-PH-101, AVICEL®-PH-103, AVICEL® RC-581, AVICEL®-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. Binder levels are from about 50% to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. In one aspect, the pharmaceutical compositions provided herein include from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; *lycopodium*; silica or silica gels, such as AEROSIL® 200 (W.R. Grace Co., Baltimore, Md.) and CAB-O-SIL® (Cabot Co. of Boston, Mass.); and mixtures thereof. In one aspect, the pharmaceutical compositions provided herein include from about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

It should be understood that many carriers and excipients may serve several functions, even within the same formulation.

In further embodiments, the pharmaceutical compositions provided herein may be provided as compressed tablets, tablet triturates, rapidly dissolving tablets, multiple compressed tablets, or enteric-coating tablets, sugar-coated, or film-coated tablets.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The capsules may also be coated as known by those of skill in the art in order to modify or sustain dissolution of the active ingredient.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

Pharmaceutical compositions provided herein are in the form of immediate or modified release dosage forms, including delayed-, sustained, pulsed-, controlled, targeted-, and programmed-release forms.

Controlled Release

In one aspect, the pharmaceutical compositions provided herein are in the form of a controlled release dosage form. As used herein, the term "controlled release" refers to a dosage form in which the rate or place of release of the active ingredient(s) is different from that of an immediate dosage form when orally administered. Controlled release dosage forms include delayed-, extended-, prolonged-, sustained-, pulsatile-, modified-, targeted-, programmed-release. The pharmaceutical compositions in controlled release dosage forms are prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, and combinations thereof. The release rate of the active ingredient(s) can also be modified by varying the particle sizes.

The pharmaceutical solid oral dosage forms including formulations described herein, which include an HDAC inhibitor (e.g. Compound 1), or a pharmaceutically acceptable salt thereof, are formulated to provide a controlled release of the HDAC inhibitor (e.g. Compound 1), or a pharmaceutically acceptable salt thereof.

In contrast to immediate release compositions, controlled release compositions allow delivery of an agent to a human over an extended period of time according to a predetermined profile. Such release rates can provide therapeutically effective levels of agent for an extended period of time and thereby provide a longer period of pharmacologic response. Such longer periods of response provide for many inherent benefits that are not achieved with the corresponding short acting, immediate release preparations. In one aspect, controlled release compositions of an HDAC inhibitor (e.g. Compound 1), or a pharmaceutically acceptable salt thereof, provide therapeutically effective levels of the HDAC inhibitor (e.g. Compound 1) for an extended period of time and thereby provide a longer period of pharmacologic response.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form may is a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. In some embodiments the polymers for use in the present invention are anionic carboxylic polymers. In other embodiments, the polymers and compatible mixtures thereof, and some of their properties, include, but are not limited to:

Shellac, also called purified lac. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonio methacrylate copolymers. The Eudragit series E, L, R, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

A particularly suitable methacrylic copolymer is Eudragit L®, particularly L-30D® and Eudragit 100-55®, manufactured by Rohm Pharma, Germany. In Eudragit L-30D®, the ratio of free carboxyl groups to ester groups is approximately 1:1. Further, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH values present in the small intestine.

In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropyl methyl cellulose phthalate, hydroxypropyl methyl cellulose acetate succinate, poly vinyl acetate phthalate, and Cotteric.

For some types of drugs, it is preferred to release the drug in "pulses," wherein a single dosage form provides for an initial dose of drug followed by a release-free interval, after which a second dose of drug is released, followed by one or more additional release-free intervals and drug release "pulses." Alternatively, no drug is released for a period of time after administration of the dosage form, after which a dose of drug is released, followed by one or more additional release-free intervals and drug release "pulses."

Pulsatile drug delivery is useful, for example, with active agents that have short half-lives are administered two or three times daily, with active agents that are extensively metabolized presystemically, and with active agents that should maintain certain plasma levels in order have optimized pharmacodynamic effects.

A pulsatile dosage form is capable of providing one or more immediate release pulses at predetermined time points after a controlled lag time or at specific sites. Pulsatile dosage forms including the formulations described herein, which include an HDAC inhibitor (e.g. Compound 1), or a pharmaceutically acceptable salt thereof, is administered using a variety of pulsatile formulations that have been described. For example, such formulations include, but are not limited to, those described in U.S. Pat. Nos. 5,011,692, 5,017,381, 5,229,135, 5,840,329, 4,871,549, 5,260,068, 5,260,069, 5,508,040, 5,567,441 and 5,837,284. In one embodiment, the controlled release dosage form is pulsatile release solid oral dosage form including at least two groups of particles, (i.e. multiparticulate) each containing the formulation described herein. The first group of particles provides a substantially immediate dose of an HDAC inhibitor (e.g. Compound 1), or a pharmaceutically acceptable salt thereof, upon ingestion by a mammal. The first group of particles can be either uncoated or include a coating and/or sealant. The second group of particles includes coated particles, which includes from about 2% to about 75%, preferably from about 2.5% to about 70%, and more preferably from about 40% to about 70%, by weight of the total dose of an HDAC inhibitor (e.g. Compound 1), or a pharmaceutically acceptable salt thereof, in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D) either alone or blended with cellulose derivatives, e.g., ethylcellulose, or non-enteric coatings having variable thickness to provide differential release of the formulation that includes an HDAC inhibitor (e.g. Compound 1), or a pharmaceutically acceptable salt thereof.

Multiparticulate Controlled Release Devices

In some embodiments, the pharmaceutical compositions described herein are multiparticulate controlled release devices, which include a multiplicity of particles, granules, or pellets, ranging from about 10 µm to about 3 mm, about 50 µm to about 2.5 mm, or from about 100 µm to about 1 mm in diameter. Such multiparticulates are made by wet-granulation, dry-granulation, extrusion/spheronization, roller-compaction, melt-congealing, by spray-coating seed cores, and combinations thereof. See, for example, *Multiparticulate Oral Drug Delivery*; Marcel Dekker: 1994; and *Pharmaceutical Pelletization Technology*; Marcel Dekker: 1989.

Other excipients or carriers as described herein are blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

Intestinal protective drug absorption system (IPDAS) is a multiparticulate tablet technology that consists of high density controlled release beads that are compressed into a tablet form. The beads may be manufactured by techniques such as extrusion spheronization and controlled release can be achieved with the use of different polymer systems to coat the resultant beads. Alternatively, the drug can also be coated onto an inert carrier such as non-pareil seeds to produce instant release multiparticulates. Controlled release can be achieved by the formation of a polymeric membrane onto these instant release multiparticulates. Once an IPDAS tablet is ingested, it rapidly disintegrates and disperses beads containing the drug in the stomach which subsequently pass into the duodenum and along the gastrointestinal tract in a controlled and gradual manner, independent of the feeding state. Release of active ingredient from the multiparticulates occurs through a process of diffusion either through the polymeric membrane and/or the micro matrix of the polymer/active ingredient formed in the extruded/spheronized multiparticulates. The intestinal protection of IPDAS is by virtue of the multiparticulate nature of the formulation which ensures wide dispersion of drug throughout the gastrointestinal tract.

Spheroidal oral drug absorption system (SODAS) is a multiparticulate technology that enables the production of customized dosage forms and responds directly to individual drug candidate needs. It can provide a number of tailored drugs release profiles including immediate release of drug followed by sustained release to give rise to a fast onset of action which is maintained for at least 12 hours. Alternatively, the opposite scenario can be achieved where drug release is delayed for a number of hours.

Programmable oral drug absorption system (PRODAS) is presented as a number of mini tablets contained in hard gelatin capsule. It thus combines the benefits of tableting technology within a capsule. It is possible to incorporate many different minitablets, each one formulated individually and programmed to release drug at different sites within the gastrointestinal tract. These combinations may include immediate release, delayed release, and/or controlled release mini tablets. It is also possible to incorporate mini tablets of different sizes so that high drug loading is possible. Their size ranges usually from 1.5-4 mm in diameter.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

Matrix Controlled Release Devices

In some embodiments, the pharmaceutical compositions provided herein is in a modified release dosage form that is fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In some embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

In one aspect, modified release dosage forms are prepared by methods known to those skilled in the art, including direct compression, dry or wet granulation followed by compression, melt-granulation followed by compression.

In some embodiments, a matrix controlled release system includes an enteric coating so that no drug is released in the stomach.

Osmotic Controlled Release Devices

In some embodiments, the pharmaceutical compositions provided herein in a modified release dosage form is fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semi-permeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semi-permeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semi-permeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semi-permeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In other embodiment pharmaceutical compositions provided herein are formulated as AMT controlled-release dosage form, which comprises an asymmetric osmotic membrane that coats a core comprising the active ingredient(s) and other pharmaceutically acceptable excipients or carriers. See U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

Multilayered Tablets

In one aspect, the controlled release formulation is in the form of a multilayered tablet. Multilayered tablets include an inert core, onto which is applied a layered of drug (plus optional excipients), followed by an enteric coating. A second layer of drug is applied onto the first enteric coating followed by a second enteric coating on the second layer of drug. The enteric coatings should ensure that the release of drug from each layer is separated in time by at least 3-6 hours.

Immediate Release

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia.). Immediate release pharmaceutical compositions include capsules, tablets, oral solutions, powders, beads, pellets, particles, and the like.

Parenteral Administration

In some embodiments, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In other embodiments, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In some embodiments, the pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

Pharmacokinetic Analysis

In one embodiment, any standard pharmacokinetic protocol is used to determine blood plasma concentration profile in humans following administration of a formulation described herein that includes an HDAC inhibitor (e.g. Compound 1), and thereby establish whether that formulation meets the pharmacokinetic and pharmacodynamic criteria set out herein. For example, a randomized single-dose crossover study is performed using a group of healthy adult human subjects. The number of subjects should be sufficient to provide adequate control of variation in a statistical analysis, and is typically about 10 or greater, although for certain purposes a smaller group suffices. Each subject receives administration at time zero of a single dose (e.g., a dose containing about 10 mg to about 300 mg of Compound 1). Blood samples are collected from each subject prior to administration (e.g., 15 minutes before) and at several intervals after administration. In certain instances, several samples are taken within the first hour and taken less frequently thereafter. Illustratively, blood samples are collected at 0 (pre-dose), 0.25, 0.5, 1, 2, 3, 4, 6, 8, 12, and 16 hours after administration. If the same subjects are to be used for study of a second test formulation, a period of at least 10 days should elapse before administration of the second formulation. Plasma is separated from the blood samples by centrifugation and the separated plasma is analyzed for the HDAC inhibitor (e.g. Compound 1) by a validated high performance liquid chromatography/tandem weight spectrometry (e.g. LC-MS/MS, LC/APCI-MS/MS) procedure such as, for example, Ramu et al., *Journal of Chromatography B*, 751 (2001) 49-59).

Any formulation giving the desired pharmacokinetic profile and pharmacodynamic effects is suitable for administration according to the present methods.

Methods of Dosing and Treatment Regimens

In one embodiment, the compositions that include an HDAC inhibitor (e.g. Compound 1) described herein are administered to humans with cancer in an amount sufficient to partially arrest the at least one of the symptoms of the cancer. The amounts effective for this use depend on the severity and course of the cancer, previous therapy, the patient's health status, weight, and response to the drugs, and/or the judgment of the treating physician.

In some embodiments, administration of the compound, compositions or therapies as described herein includes chronic administration. In specific embodiments, chronic administration is utilized in certain instances wherein the patient's condition does not improve and/or upon the doctor's discretion. In certain embodiments, chronic administration includes administration for an extended period of time, including, e.g., throughout the duration of the patient's life in order to ameliorate or otherwise control or limit the symptoms of the cancer.

In some embodiments, administration of the compounds, compositions or therapies described herein is given continuously.

In some embodiments, the dose of drug being administered is temporarily suspended for a certain length of time (i.e., a "drug holiday"). The length of the drug holiday varies between 4 days and 9 days.

In one aspect, pharmaceutical compositions that include an HDAC inhibitor (e.g. Compound 1) are administered to humans with cancer in cycles that include consecutive days of daily administration of an HDAC inhibitor (e.g. Compound 1) followed by consecutive days of no administration of an HDAC inhibitor (e.g. Compound 1). Such a dosing schedule of an HDAC inhibitor (e.g. Compound 1) allows for a pharmacodynamic response to an HDAC inhibitor (e.g. Compound 1) to be achieved while limiting the incidence of Grade 4 thrombocytopenia. Grade 4 thrombocytopenia typically includes instances when the human has a platelet count less than 25,000 per $mm^2$. In one aspect, pharmaceutical compositions that include an HDAC inhibitor (e.g. Compound 1) are administered to humans with cancer in cycles that include 5, 6, 7, 8 or 9 consecutive days of daily administration of an HDAC inhibitor (e.g. Compound 1) followed by 5, 6, 7, 8 or 9 consecutive days of no administration of an HDAC inhibitor (e.g. Compound 1).

If the human is receiving concurrent treatment with a second drug other than an HDAC inhibitor (e.g. Compound 1), then treatment with the second drug is not halted on the days that an HDAC inhibitor (e.g. Compound 1) is not administered. In one aspect, if the human is receiving concurrent treatment with a second drug other than an HDAC inhibitor (e.g. Compound 1), then treatment with the second drug is halted on the days that the HDAC inhibitor (e.g. Compound 1) is not administered.

In one aspect, immediate release formulations of an HDAC inhibitor (e.g. Compound 1) are administered to humans twice a day. In one aspect, immediate release formulations of an HDAC inhibitor (e.g. Compound 1) are administered to humans twice a day, the two immediate release doses being administered about 3 hours to about 6 hours apart.

In one aspect, controlled release formulations of an HDAC inhibitor (e.g. Compound 1) are administered to humans once a day. In one aspect, controlled release formulations of an HDAC inhibitor (e.g. Compound 1) that are administered to humans once a day provide the same amount of an HDAC inhibitor (e.g. Compound 1) that would be obtained from daily dosing with two immediate release formulations of the HDAC inhibitor (e.g. Compound 1). In one aspect, controlled release formulations of an HDAC inhibitor (e.g. Compound 1) that are administered to humans once a day provide the same amount of an HDAC inhibitor (e.g. Compound 1) that would be obtained from daily dosing with two immediate release formulations of an HDAC inhibitor (e.g. Compound 1), wherein the two immediate release doses are administered about 3 hours to about 6 hours apart.

Daily Doses

In certain embodiments, the amount of an HDAC inhibitor (e.g. Compound 1), or a pharmaceutically acceptable salt thereof, that is administered varies depending upon factors including, by way of non-limiting example, the type of formulation utilized, the type of cancer and its severity, the identity (e.g., weight, age) of the human, and/or the route of administration. In various embodiments, the desired dose is conveniently presented in a single dose or in divided doses administered simultaneously (or over a short period of time) or at appropriate intervals, for example as two, three, four or more sub-doses per day.

In some embodiments, the pharmaceutical compositions described herein are in unit dosage forms suitable for single administration of precise dosage amounts. In unit dosage form, the formulation is divided into unit doses containing appropriate quantities of an HDAC inhibitor (e.g. Compound 1), or a pharmaceutically acceptable salt thereof. In one embodiment, the unit dosage is in the form of a package containing discrete quantities of the formulation. Non-limiting examples are packaged tablets or capsules, and powders in vials or ampoules. In one embodiment, aqueous suspension compositions are packaged in single-dose non-reclosable containers. Alternatively, multiple-dose reclosable containers are used, in which case it is typical to include a preservative in the composition.

Daily amounts of Compound 1, or a pharmaceutically acceptable salt thereof, which are administered to humans range from about 10 mg/mm$^2$ to about 200 mg/mm$^2$. In one aspect, daily amounts of Compound 1, or a pharmaceutically acceptable salt thereof, which are administered to humans range from about 30 mg/mm$^2$ to about 90 mg/mm$^2$. In one aspect, daily amounts of Compound I, or a pharmaceutically acceptable salt thereof, which are administered to humans range include about 20 mg/mm$^2$, about 30 mg/mm$^2$, about 40 mg/mm$^2$, about 50 mg/mm$^2$, about 60 mg/mm$^2$, about 70 mg/mm$^2$, about 80 mg/mm$^2$, or about 90 mg/mm$^2$.

In one aspect, Compound 1, or a pharmaceutically acceptable salt thereof, is administered as an immediate release formulation that includes about 20 mg/mm$^2$, about 30 mg/mm$^2$, about 40 mg/mm$^2$, about 50 mg/mm$^2$, about 60 mg/mm$^2$, about 70 mg/mm$^2$, about 80 mg/mm$^2$, or about 90 mg/mm$^2$ of Compound 1. In one aspect, Compound 1, or a pharmaceutically acceptable salt thereof, is administered as an immediate release formulation that includes about 30 mg/mm$^2$ of Compound 1, or a pharmaceutically acceptable salt thereof.

In one aspect, an HDAC inhibitor (e.g. Compound 1) is administered as two immediate release formulations, where the second immediate release formulation is administered about 4 hours to about 6 hours after the first dose is administered. Each immediate release formulation includes the same amount of the HDAC inhibitor (e.g. Compound 1), or a pharmaceutically acceptable salt thereof, as described herein. The two immediate release formulations provide sustained effective plasma levels of an HDAC inhibitor (e.g. Compound 1) that are needed for therapeutic and pharmacodynamic effect while minimizing side effects. In one aspect, sustained effective plasma levels of an HDAC inhibitor (e.g. Compound 1) are maintained for about 6 hours to about 8 hours.

In one aspect, Compound 1, or a pharmaceutically acceptable salt thereof, is administered as a controlled release formulation that includes about 30 mg/mm$^2$, about 40 mg/mm$^2$, about 50 mg/mm$^2$, about 60 mg/mm$^2$, about 70 mg/mm$^2$, about 80 mg/mm$^2$, or about 90 mg/mm$^2$ of Compound 1. In one aspect, Compound 1, or a pharmaceutically acceptable salt thereof, is administered as a controlled release formulation that includes about 60 mg/mm$^2$ of Compound 1, or a pharmaceutically acceptable salt thereof.

In one aspect, immediate release formulations include about 10 mg to about 300 mg of Compound 1. In one aspect, immediate release formulations include about 20 mg to about 200 mg of Compound 1.

In one aspect, controlled release formulations include about 20 mg to about 600 mg of Compound 1. In one aspect, immediate release formulations include about 40 mg to about 400 mg of Compound 1.

Cancers

In one aspect, an HDAC inhibitor (e.g. Compound 1), or a pharmaceutically acceptable salt thereof, is used in the treatment of cancer in a human. In one aspect, an HDAC inhibitor (e.g. Compound 1), or a pharmaceutically acceptable salt thereof, is used in the treatment of a hematological cancer in a human. In one aspect, an HDAC inhibitor (e.g. Compound 1), or a pharmaceutically acceptable salt thereof, is used in the treatment of a solid tumor in a human.

Hematological cancers include cancers of the blood or bone marrow, such as leukemia or lymphoma.

A lymphoma is a cancer that begins in cells of the immune system. There are two basic categories of lymphomas. One kind is Hodgkin lymphoma, which is marked by the presence of a type of cell called the Reed-Sternberg cell. The other category is non-Hodgkin lymphomas, which includes a large, diverse group of cancers of immune system cells. Non-Hodgkin lymphomas can be further divided into cancers that have an indolent (slow-growing) course and those that have an aggressive (fast-growing) course.

A leukemia is a cancer that starts in blood-forming tissue such as the bone marrow and causes large numbers of blood cells to be produced and enter the bloodstream.

In one aspect, the cancer is a solid tumor or a lymphoma or leukemia. In one aspect, the cancer is a carcinoma, a sarcoma, a lymphoma, a leukemia, a germ cell tumor, a blastic tumor or blastoma.

In one aspect, an HDAC inhibitor (e.g. Compound 1), or a pharmaceutically acceptable salt thereof, is used in the treatment of a cancer selected from: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; Adrenal glands: neuroblastoma; gallbladder carcinomas.

In one aspect, the cancer is breast cancer, colon cancer, colorectal carcinomas, non-small cell lung cancer, small-cell lung cancer, liver cancer, ovarian cancer, prostate cancer, uterine cervix cancer, urinary bladder cancer, gastric carcinomas, gastrointestinal stromal tumors, pancreatic cancer, germ cell tumors, mast cell tumors, neuroblastoma, mastocytosis, testicular cancers, glioblastomas, astrocytomas, lymphomas, melanoma, myelomas, acute myelocytic leukemia (AML), acute lymphocytic leukemia (ALL), myelodysplastic syndrome, and chronic myelogenous leukemia (CML).

In one aspect, the cancer is a lymphoma. In one aspect, the lymphoma is a B cell lymphoma, T cell lymphoma, Hodgkin's lymphoma, or non-Hodgkin's lymphoma.

In one aspect, the cancer is a T-cell lymphoma or leukemia.

In one aspect, the T-cell lymphoma is peripheral T cell lymphoma. In another aspect, the T-cell lymphoma or leukemia is T cell lymphoblastic leukemia/lymphoma. In yet another aspect, the T-cell lymphoma is cutaneous T cell lymphoma. In another aspect, the T-cell lymphoma is adult T cell lymphoma. In one aspect, the T-cell lymphoma is peripheral T cell lymphoma, lymphoblastic lymphoma, cutaneous T cell lymphoma, NK/T-cell lymphoma, or adult T cell leukemia/lymphoma.

In one embodiment, the cancer is a sarcoma. A sarcoma is a cancer that begins in the muscle, fat, fibrous tissue, blood vessels, or other supporting tissue of the body. Sarcomas include any one of the following: alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, malignant fibrous histiocytoma, neurofibrosarcoma, rhabdomyosarcoma, synovial sarcoma, askin's tumor, ewing's, malignant hemangioendothelioma, malignant schwannoma, osteosarcoma, chondrosarcoma.

In one aspect, an HDAC inhibitor (e.g. Compound 1), or a pharmaceutically acceptable salt thereof, is used in the treatment of a soft tissue sarcoma in a human.

In one aspect, an HDAC inhibitor (e.g. Compound 1), or a pharmaceutically acceptable salt thereof, is used in the treatment of myelodysplastic syndrome (MDS) in a human.

In one aspect, an HDAC inhibitor (e.g. Compound 1), or a pharmaceutically acceptable salt thereof, is used in the treatment of chronic myelogenous leukemia (CML) in a human.

In one aspect, an HDAC inhibitor (e.g. Compound 1), or a pharmaceutically acceptable salt thereof, is used in the treatment of non-Hodgkin lymphoma in a human. In one aspect, an HDAC inhibitor (e.g. Compound 1), or a pharmaceutically acceptable salt thereof, is used in the treatment of Hodgkin Disease in a human.

In one aspect, an HDAC inhibitor (e.g. Compound 1), or a pharmaceutically acceptable salt thereof, is used in the treatment of multiple myeloma in a human.

In one aspect, an HDAC inhibitor (e.g. Compound 1), or a pharmaceutically acceptable salt thereof, is used in the treatment of chronic lymphocytic leukemia. In one aspect, an HDAC inhibitor (e.g. Compound 1), or a pharmaceutically acceptable salt thereof, is used in the treatment of acute lymphocytic leukemia.

In one aspect, an HDAC inhibitor (e.g. Compound 1), or a pharmaceutically acceptable salt thereof, is used in the treatment of a solid tumor in a human.

In one aspect, an HDAC inhibitor (e.g. Compound 1), or a pharmaceutically acceptable salt thereof, is used in the treatment of a sarcoma in a human.

Combination Therapies

In one embodiment, the compositions and methods described herein are also used in conjunction with other therapeutic reagents that are selected for their particular usefulness against the cancer that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In certain embodiments, the particular choice of compounds used depends on the diagnosis of the attending physicians and their judgment of the condition of the patient and the appropriate treatment protocol. In various embodiments, the compounds are administered concurrently (e.g., simultaneously, essentially simultaneously or within the same treatment protocol) or sequentially, depending upon the nature of the cancer, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

In one embodiment, it is understood that the dosage regimen to treat the cancer is modified in accordance with a variety of factors. These factors include the type of cancer from which the human suffers, as well as the age, weight, sex, diet, and medical condition of the human. Thus, in one embodiment, the dosage regimen actually employed varies widely and therefore deviates from the dosage regimens set forth herein. In certain embodiments, treatment of a cancer with a combination of an HDAC inhibitor (e.g. Compound 1) and a second agent allows for the effective amount of the HDAC inhibitor (e.g. Compound 1) and/or the second agent to be decreased.

The formulations described herein are administered and dosed in accordance with good medical practice, taking into account the clinical condition of the individual patient, the method of administration, scheduling of administration, and other factors known to medical practitioners.

Contemplated pharmaceutical compositions provide a therapeutically effective amount of an HDAC inhibitor (e.g. Compound 1) enabling, for example, once-a-day, twice-a-day, three times a day, etc. administration. In one aspect, pharmaceutical compositions provide an effective amount of an HDAC inhibitor (e.g. Compound 1) enabling once-a-day dosing.

In certain instances, it is appropriate to administer an HDAC inhibitor (e.g. Compound 1) in combination with another therapeutic agent.

In certain embodiments, the therapeutic effectiveness of an HDAC inhibitor (e.g. Compound 1) is enhanced by administration of an adjuvant (i.e., by itself the adjuvant has minimal therapeutic benefit, but in combination with another therapeutic agent, the overall therapeutic benefit to the patient is enhanced). In some embodiments, the benefit experienced by a patient is increased by administering an HDAC inhibitor (e.g. Compound 1) with another therapeutic agent (which also includes a therapeutic regimen) that also has therapeutic benefit. In specific embodiments, in a treatment for cancer involving administration of an HDAC inhibitor (e.g. Compound 1), increased therapeutic benefit results by also providing the patient with other therapeutic agents or therapies for cancer. In various embodiments, administration to an individual of an HDAC inhibitor (e.g. Compound 1) in combination with a second agent provides the individual with, e.g., an additive or synergistic benefit.

Therapeutically-effective dosages vary when the drugs are used in treatment combinations. Determination of therapeutically-effective dosages of drugs and other agents when used in combination treatment regimens is achieved in any manner. For example, the use of metronomic dosing, i.e., providing more frequent, lower doses in order to minimize toxic side effects can be utilized. In certain instances, the combination therapy allows for either or both of the an HDAC inhibitor (e.g. Compound 1) and the second agent to have a therapeutically effective amount that is lower than would be obtained when administering either agent alone.

A combination treatment regimen encompasses, by way of non-limiting example, treatment regimens in which administration of an HDAC inhibitor (e.g. Compound 1) is initiated prior to, during, or after treatment with a second agent, and continues until any time during treatment with the second agent or after termination of treatment with the second agent. It also includes treatments in which an HDAC inhibitor (e.g. Compound 1) and the second agent being used in combination are administered simultaneously or at different times and/or at decreasing or increasing intervals during the treatment period. Combination treatment further includes periodic treatments that start and stop at various times to assist with the clinical management of the patient.

In any case, the multiple therapeutic agents (one of which is an HDAC inhibitor (e.g. Compound 1)) are administered in any order, including, e.g., simultaneously. If administration is simultaneous, the multiple therapeutic agents are provided, in various embodiments, in a single, unified form, or in multiple forms (by way of example only, either as a single pill or as two separate pills). In various embodiments, one of the therapeutic agents is given in multiple doses, or both are given as multiple doses. In certain embodiments wherein administration of the multiple agents is not simultaneous, the timing between administration of the multiple agents is of any acceptable range including, e.g., from more than zero weeks to less than four weeks. In some embodiments, the combination methods, compositions and formulations include an HDAC inhibitor (e.g. Compound 1), a second agent and a third agent. In further embodiments, additional agents are also utilized.

In certain embodiments, the initial administration is via oral administration, such as, for example, a pill, a capsule, a tablet, a solution, a suspension, and the like, or combination thereof. In certain embodiments, an HDAC inhibitor (e.g. Compound 1) is administered as soon as is practicable after the onset of a cancer is detected or suspected, and for a length of time necessary for the treatment of the cancer. In certain embodiments, administration of the agents, formulations or compositions described herein is for a length of time necessary for the treatment of the cancer including, by way of non limiting example, for at least 2 weeks, at least 1 month, or more than 1 month.

In one aspect, an HDAC inhibitor (e.g. Compound 1) is administered to a human in combination with at least one additional therapeutic agent selected from among DNA-damaging agents; topoisomerase I or II inhibitors; alkylating agents; PARP inhibitors; proteasome inhibitors; RNA/DNA antimetabolites; antimitotics; immunomodulatory agents; antiangiogenics; aromatase inhibitors; hormone-modulating agents; apoptosis inducing agents; kinase inhibitors; monoclonal antibodies; abarelix; ABT-888; aldesleukin; aldesleukin; alemtuzumab; alitretinoin; allopurinol; altretamine; amifostine anastrozole; arsenic trioxide; asparaginase; azacitidine; AZD-2281; bendamustine; bevacizumab; bexarotene; bleomycin; bortezomib; BSI-201; busulfan; busulfan; calusterone; capecitabine; carboplatin; carfilozib; carmustine; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine; denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzamab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; meclorethamine; megestrol acetate; melphalan; mercaptopurine; methotrexate; methoxsalen; mitomycin C; mitomycin C; mitotane; mitoxantrone; nandrolone phenpropionate; nelarabine; NPI-0052; nofetumomab; oprelvekin; oxaliplatin; paclitaxel; paclitaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium;

procarbazine; quinacrine; RAD001; rasburicase; rituximab; sargramostim; Sargramostim; sorafenib; streptozocin; sunitinib malate; tamoxifen; temozolomide; teniposide; testolactone; thalidomide; thioguanine; thiotepa; topotecan; toremifene; tositumomab; tositumomab/I-131 tositumomab; trastuzumab; tretinoin; uracil Mustard; valrubicin; vinblastine; vincristine; vinorelbine; vorinostat; zoledronate; and zoledronic acid.

In one aspect, an HDAC inhibitor (e.g. Compound 1) is administered to a human in combination with a topoisomerase inhibitor, tubulin interactor, DNA-interactive agent, DNA-alkylating agent, and/or platinum complex.

In one aspect, an HDAC inhibitor (e.g. Compound 1) is administered to a human in combination with oxaliplatin, tyrosine kinase inhibitor, irinotecan (CPT-11), azacitidine, fludarabine, or bendamustine.

Tyrosine kinase inhibitors include, but are not limited to, erlotinib, gefitinib, lapatinib, vandetanib, neratinib, lapatinib, neratinib, axitinib, sunitinib, sorafenib, lestaurtinib, semaxanib, cediranib, imatinib, nilotinib, dasatinib, bosutinib, lestaurtinib, vatalanib and soratinib.

In one aspect, an HDAC inhibitor (e.g. Compound 1) is administered to a human in combination with a DNA damaging anti-cancer agent and/or radiation therapy.

DNA damaging anti-cancer agents and/or radiation therapy include, but is not limited to, ionizing radiation, radiomimetic drugs, monofunctional alkylators (e.g. alkylsulphonates, nitrosoureas, temozolomide), bifunctional alkylators (nitrogen mustard, mitomycin C, cisplatin), antimetabolites (e.g. 5-fluorouracil, thiopurines, folate analogues), topoisomerase inhibitors (e.g. camptothecins, etoposide, doxorubicin), replication inhibitors (e.g. aphidicolin, hydroxyurea), cytotoxic/cytostatic agents, antiproliferative agents, prenyl-protein transferase inhibitors, nitrogen mustards, nitroso ureas, angiogenesis inhibitors, inhibitors of cell proliferation and survival signaling pathway, apoptosis inducing agents, agents that interfere with cell cycle checkpoints, biphosphonates, or any combination thereof.

In one aspect, an HDAC inhibitor (e.g. Compound 1) is administered to a human in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

In one aspect, an HDAC inhibitor (e.g. Compound 1) is administered to a human in combination with anti-emetic agents to treat nausea or emesis, including acute, delayed, late-phase, and anticipatory emesis, which may result from the use of an HDAC inhibitor (e.g. Compound 1), alone or with radiation therapy. Anti-emetic agents include neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others such as disclosed in U.S. Pat. Nos. 2,789,118; 2,990,401; 3,048,581; 3,126,375; 3,929,768; 3,996,359; 3,928,326 and 3,749,712), dopamine antagonists (such as, domperidone, droperidol, haloperidol, chlorpromazine, promethazine, prochlorperazine, metoclopramide), antihistamines (H1 histamine receptor antagonists, such as cyclizine, diphenhydramine, dimenhydrinate, meclizine, promethazine, hydroxyzine), cannabinoids (such as *cannabis*, marinol, dronabinol), and others (such as trimethobenzamide; ginger, emetrol, propofol).

In one aspect, an HDAC inhibitor (e.g. Compound 1) is administered to a human in combination with an anti-emesis agent selected from among a neurokinin-1 receptor antagonist, a 5HT3 receptor antagonist and a corticosteroid.

In one aspect, an HDAC inhibitor (e.g. Compound 1) is administered to a human in combination with an agent useful in the treatment of anemia. Such an anemia treatment agent is, for example, a continuous eythropoiesis receptor activator (such as epoetin-α).

In one aspect, an HDAC inhibitor (e.g. Compound 1) is administered to a human in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, an HDAC inhibitor (e.g. Compound 1) is administered to a human in combination with an inhibitor of at least one CYP enzyme. In situations where the HDAC inhibitor is metabolized by one or more CYP enzymes, coadministration with a CYP inhibitor reduces the in vivo metabolism of the HDAC inhibitor and improves the pharmacokinetic properties of the HDAC inhibitor.

Other combination therapies are disclosed in WO 08/082,856 and WO 07/109,178, both of which are herein incorporated by reference in their entirety.

Radiation Therapy

In one aspect, an HDAC inhibitor (e.g. Compound 1) is administered in combination with radiation therapy. Radiation therapy, also called radiotherapy, is the treatment of cancer and other diseases with ionizing radiation. Ionizing radiation deposits energy that injures or destroys cells in an area being treated (a "target tissue") by damaging their genetic material, making it impossible for these cells to continue to grow. Although radiation damages both cancer cells and normal cells, the latter are better able to repair themselves and function properly. Radiotherapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α,β, and γ radiation and ultra violet light. Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X.

Provided are methods of using an HDAC inhibitor (e.g. Compound 1) to reduce side effect caused by at least one other therapeutic treatment, such as radiation-induced normal tissue fibrosis or chemotherapy-induced tissue necrosis, and the methods provided herein also synergistically inhibit tumor cell growth with radiotherapy and other anti-cancer agents.

RAD51

DNA damage causes chromosomal instability, oncogensis, cell death, and severe dysfunction of cells. The DNA repair system is crucially important for the survival of living cells. The two major DNA repair mechanisms involved in the repair of double stranded DNA breaks are homologous recombination (HR) and non-homologous end joining (NHEJ). The eukaryotic RAD51 gene is an ortholog of *Escherichia coli* RecA, and the gene product RAD51 protein plays a central role in homologous recombination.

Many therapeutic treatments, such as anti-cancer agents, exert their therapeutic effects through their capability of producing DNA damage to cells. If the cells, such as cancer cells, have active DNA repair mechanisms, the therapeutic effects of such treatments may be compromised and high dosages may be needed for achieving the desired therapeutic effects.

In one aspect, an HDAC inhibitor (e.g. Compound 1) is used to decrease cellular DNA repair activity in a human with cancer.

In one aspect, presented are methods of treating cancer by using an HDAC inhibitor (e.g. Compound 1) to decrease cellular DNA repair activity in combination therapy. Described are methods of combination therapy where an HDAC inhibitor (e.g. Compound 1) interferes with a DNA repairing mechanism involving RAD51 or BRCA1.

In one aspect are methods for treating cancers associated with a defect in non-homologous end joining of DNA, comprising: (a) administering to a human having a cancer associated with a defect in non-homologous end joining of DNA, a therapeutically effective amount of an HDAC inhibitor (e.g. Compound 1); and (b) administering to the human a treatment capable of damaging cellular DNA.

The defect in non-homologous end joining of DNA comprises a defect in a gene selected from the group consisting of: Ku70, Ku80, Ku86, Ku, PRKDC, LIG4, XRCC4, DCLRE1C, and XLF. In one aspect, the cancer is selected from Burkitt's lymphoma, chronic myelogenous leukemia, and B-cell lymphoma. In one aspect, the cancer is described herein.

In one aspect, an HDAC inhibitor (e.g. Compound 1) is used in the treatment of an alternative lengthening of telomere (ATL) positive cancer in a human.

Additional combination therapies, treatment strategies, and the like that include inhibiting RAD51 activity (e.g. an HDAC inhibitor (e.g. Compound 1)) are disclosed in US patent publication number 20080153877 and WO 08/082,856 (both of which are herein incorporated by reference).

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, pumps, bags, containers, bottles, and any packaging material suitable for a selected formulation and intended mode of administration and treatment. A wide array of formulations of the compounds and compositions provided herein are contemplated.

Such kits optionally comprise an identifying description or label or instructions relating to its use in the methods described herein.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert.

EXAMPLES

These examples are provided for illustrative purposes only and not to limit the scope of the claims provided herein.
Synthesis of Compound 1, HCl
Compound 1, HCl was prepared as outlined in Example 7 of U.S. Pat. No. 7,276,612, the contents of which are incorporated herein by reference in its entirety.

Example 1

IV Solution of Compound 1

Compound 1 was formulated as an intravenous (IV) solutions for initial clinical trials in humans. The IV solution is an aqueous solution formulation intended for infusion administration after dilution with isotonic saline. Each single use vial contains 25 mL of a 5 mg/mL (0.5%) solution of Compound 1 in isotonic saline and 50 mM lactate buffer, pH 4.0-4.5. All the excipients in the clinical formulations are compendial and are commonly used in parenteral formulations. The quantitative composition of the formulation is given in Table 1. The recommended storage condition is 2-8° C.

TABLE 1

| Quantitative Composition of IV Solution (5 mg/mL) | | | |
|---|---|---|---|
| Ingredient | Percent (% w/w) | mg/g (w/w) | Typical Batch (57.5 kg) |
| Compound 1 (anhydrous, free base) | 0.5 | 5.0 | 0.288 kg |
| Lactic acid | 0.45 | 4.5 | 0.259 kg |
| Sodium chloride | 0.665 | 6.65 | 0.382 kg |
| Water for injection | — | — | Q.S. to volume |
| 1N sodium hydroxide* and/or 1N hydrochloric acid* Q.S. to pH 4.0-4.5 ± 0.2 | — | — | Q.S. to pH |

Example 2

Immediate Release Capsules

Immediate release capsules are formulated by mixing the HCl salt of Compound 1, with microcrystalline cellulose, lactose, and magnesium stearate and then adding the mixture into gelatin capsules (see Table 2). The capsules are manufactured in two strengths. A 20 mg dosage strength includes 20 mg of the HCl salt of Compound 1 in a size 4 Swedish orange hard gelatin capsule. A 100 mg dosage strength includes 100 mg of the HCl salt of Compound 1 in a size 2 dark green hard gelatin capsule. The capsules are packaged in 30 cc HDPE bottles and sealed with an induction seal and capped with a child resistant screw top cap. The 20 mg dosage strength is packaged at 50 capsules per bottle. The 100 mg dosage strength is packaged at 30 capsules per bottle. The bottles are stored at controlled room temperature 20-25° C. (68-77° F.).

TABLE 2

Immediate Release Capsules

| Component | Quality Standard | Mg/Capsule | | Function |
|---|---|---|---|---|
| Compound 1, HCl | Manufacturer's Specification | 20 mg[a] | 100 mg[a] | Active Pharmaceutical Ingredient |
| Avicel PH113 (microcrystalline cellulose) | NF | 68 mg | 76 mg | Disintegrant |
| Lactose, Anhydrous | NF | 15.7 mg | 17.6 mg | Diluent |
| Magnesium Stearate | NF | 1.3 mg | 1.5 mg | Lubricant |

[a]The quantity of Compound 1 per capsule is adjusted for water content and purity.

Example 3

Multiparticulate Pulsatile Formulation with Timed Release 80 grams of sodium chloride and 24 grams of polyvinylpyrrolidone are dissolved in 1.2 kilograms of water and 400 grams of pulverized Compound 1, HCl are suspended therein.

In a fluidized bed coater, 400 grams of starch/sugar seeds (30/50 mesh) are suspended in warm air and spray coated with the Compound 1, HCl suspension until the seeds are uniformly coated with the desired drug potency.

Magnesium stearate in isopropyl alcohol is mixed with Eudragit NE30D (Rohm Pharma of Weiterstadt, Germany), in a proportion of two to 1 of dried polymer to magnesium stearate. A sufficient amount of the polymer suspension is sprayed onto the active cores to provide a particular film coating thickness to achieve a particular lag time and rate of release for a population of pellets. The final coated pellets are dried at 50° C. for 2 hours to assure complete removal of moisture to stabilize the core contents.

The procedure is repeated with at least one more batch using a different coating thickness to have a different lag time and rate of release. In this example, two populations are prepared, one with a 10% weight gain and one with a 30% weight gain of coating. Unit doses are prepared by mixing the two populations together in predetermined proportions and filling capsules with the mixture.

After oral administration of a unit dose to a human, the first population of pellets does not begin to release Compound 1, HCl until an initial lag time of about 2-3 hours has elapsed. The second population of pellets does not begin to release Compound 1, HCl until an initial lag time of about 6-7 hours has elapsed. The mean release time (the time when half of the drug has been released) of each population of pellets should be separated from one another by at least 3-4 hours.

Fluidized bed coaters are well known in the art, however other coating apparatus and methods well known in the art may be used instead.

Example 4

Alternative Multiparticulate Pulsatile Formulation with Timed Release

The active cores are prepared as in Example 3. Magnesium stearate and triacetin plasticizer are mixed with Eudragit RS 30D suspension in a dry weight ratio of 1:0.6:2. The polymer suspension is coated on the cores as in Example 3, preparing a plurality of populations, each having a particular coating thickness to provide a particular lag time and rate of release of drug in an aqueous environment of use.

The different population of pellets are mixed and the mixture used to fill capsules as described in Example 3.

Example 5

Pulsatile Formulation—Tablets in Capsule

A pulsatile release dosage form for administration of Compound 1, HCl salt, is prepared by (1) formulating two individual compressed tablets, each having a different release profile, followed by (2) encapsulating the two tablets into a gelatin capsule and then closing and sealing the capsule. The components of the two tablets are as follows.

TABLE 3

Tablet 1 (Without Coating)

| Component | Function | Amount per tablet |
|---|---|---|
| Compound 1, HCl | Active agent | 20.0 mg |
| Dicalcium phosphate dihydrate | Diluent | 38.5 mg |
| Microcrystalline cellulose | Diluent | 38.5 mg |
| Sodium starch glycolate | Disintegrant | 2.4 mg |
| Magnesium Stearate | Lubricant | 0.6 mg |

The tablets are prepared by wet granulation of the individual drug particles and other core components as may be done using a fluid-bed granulator, or are prepared by direct compression of the admixture of components. Tablet 1 is an immediate release dosage form, releasing the active agent completely within 1-2 hours following administration.

Half of the immediate release tablets are coated with Delayed Coating No. 1 to provide Tablet 2. Tablet 2 delays the release of Compound 1, HCl by about 3-5 hours after administration. Half of the immediate release tablets are coated with Delayed Coating No. 2 to provide Tablet 3. Tablet 3 delays the release of Compound 1, HCl by about 4-9 hours after administration. The coating is carried out using conventional coating techniques such as spray-coating or the like.

TABLE 4

Tablet 2 (with Coating)

| Component | Function | Weight |
|---|---|---|
| Tablet 1 | "Core" containing the active agent | 100.0 mg |
| Eudragit RS30D | Delayed release coating material | 8.0 mg |
| Talc | Coating component | 6.0 mg |
| Triethyl citrate | Coating component | 2.0 mg |

TABLE 5

Tablet 3 (with Coating)

| Component | Function | Weight |
|---|---|---|
| Tablet 1 | "Core" containing the active agent | 100.0 mg |
| Eudragit RS30D | Delayed release coating material | 12 mg |
| Talc | Coating component | 7 mg |
| Triethyl citrate | Coating component | 3.0 mg |

Oral administration of the capsule to a patient should result in a release profile having two pulses, with initial release of Compound 1, HCl occurring about 3-5 hours following administration, and release of Compound 1, HCl from the second tablet occurring about 7-9 hours following administration.

Example 6

Pulsatile Formulation—Beads in Capsule or Tablet

The method of Example 5 is repeated, except that drug-containing beads are used in place of tablets. Immediate release beads are prepared by coating an inert support material such as lactose with the drug. The immediate release beads are coated with an amount of enteric coating material sufficient to provide a drug release-free period of about 3-5 hours. A second fraction of beads is prepared by coating immediate release beads with a greater amount of enteric coating material, sufficient to provide a drug release-free period of about 7-9 hours. The two groups of coated beads are encapsulated as in Example 5, or compressed, in the presence of a cushioning agent, into a single pulsatile release tablet.

Example 7

Sustained Release Tablet

Sustained release tablets of Compound 1, HCl are prepared by first preparing a sustained release excipient. The sustained release excipient is prepared by dry blending the requisite amounts of xanthan gum, locust bean gum, a pharmaceutically acceptable hydrophobic polymer and an inert diluent in a high-speed mixer/granulator for 2 minutes. While running choppers/impellers, the water was added and the mixture was granulated for another 2 minutes. The granulation was then dried in a fluid bed dryer to a loss on drying weight ("LOD") of between 4 and 7%. The granulation was then milled using 20 mesh screens. The ingredients of the sustained release excipients are set forth in Table 6 below:

TABLE 6

Sustained Release Excipient Mixture

| Component | % by Weight |
|---|---|
| Xanthan Gum | 10 |
| Locust Bean Gum | 10 |
| Carboxymethylcellulose | 30 |
| Dextrose | 50 |
| Water | 23* |

*removed during processing

Next, the sustained release excipient prepared as detailed above is dry blended with a desired amount of Compound 1, HCl, in a V-blender for 10 minutes. A suitable amount of tableting lubricant Pruv® (sodium stearyl fumarate, NF) for the following examples is added and the mixture is blended for another 5 minutes. This final mixture is compressed into tablets, each tablet containing 10% by weight, of Compound 1, HCl. The tablets produced weighed 500 mg (Diameter is ⅜ inches; hardness is 2.6 Kp). The proportions of the tablets are set forth in Table 7 below.

TABLE 7

Sustained Release Tablets

| Component | % by Weight |
|---|---|
| sustained release excipient mixture of Table 6 | 88.5 |
| Compound 1, HCl | 10 |
| Sodium Stearyl Fumarate | 1.5 |

Dissolution tests are then carried out on the tablets. The dissolution tests are conducted in an automated USP dissolution apparatus (Paddle Type II, pH 7.5 buffer, 50 rpm in 500 mL.). The tablets should release about 30% of Compound 1, HCl by 2 hours, followed by a sustained release such that about 98% of Compound 1, HCl is released at the end of 12 hours.

Example 8

Coated Sustained Release Tablet

A sustained release excipient was prepared as described above by dry blending the requisite amounts of xanthan gum, locust bean gum and an inert diluent. An extra 2 minutes of granulation was used after the addition of the components (for 4 total minutes of post-addition granulation). Ethylcellulose aqueous dispersion was substituted for water in the above methods. The components of the sustained release excipient is described in Table 8.

TABLE 8

Sustained Release Excipient

| Component | % by Weight |
|---|---|
| Xanthan Gum | 12 |
| Locust Bean Gum | 18 |
| Dextrose | 65 |
| Ethylcellulose Aqueous Dispersion | 5* |

*Ethylcellulose Aqueous Dispersion contains approx. 25% by weight of solids. The amount added to the formulation (i.e. 5%) is solids only.

The xanthan gum and locust bean gum are dry blended in a V-blender for 10 minutes, the dextrose is added and the mixture blended for another 5 minutes. The ethylcellulose aqueous dispersion is then added, followed by an additional 5 minutes of blending. The resulting granulation is then compressed into tablets with sodium stearyl fumarate, as a tableting lubricant. The tablets are then coated with additional ethylcellulose aqueous dispersion. To accomplish this, ethylcellulose (Surelease®, 400 g) is mixed with water (100 g) to form an aqueous suspension. Thereafter, the tablets are coated in a Keith Machinery coating pan (diameter 350 mm; pan speed 20 rpm; spray-gun nozzle 0.8 mm; tablets bed temperature 40°-50° C.; charge per batch 1 kg; dry air—Conair Prostyle 1250, 60°-70° C.). The tablets are coated to a weight gain of about 5%. The tablets should weigh about 500 mg. The proportions of the tablets are set forth in Table 9 below:

TABLE 9

Coated Sustained Release Tablets

| Component | % by Weight |
| --- | --- |
| sustained release excipient mixture of Table 8 | 83.5 |
| Compound 1, HCl | 10 |
| Ethylcellulose | 5 |
| Sodium Stearyl Fumarate | 1.5 |

The dissolution tests are conducted in an automated USP dissolution apparatus in such a way as to model passage through the gastrointestinal tract. The coated tablets should not release more than 10% Compound 1, HCl during the first 1-2 hours, and then should release Compound 1, HCl at a steady rate such that about 90% to 100% of Compound 1, HCl is released after 12 hours.

Example 9

In Vitro Release Profiles

The dissolution profiles are obtained using the United States Pharmacopeia Apparatus I at 37° C. and 100 RPM. The dissolution media is varied with time beginning with 0.1N HCl for 0-2 hours. From 2 to 4 hours the media is pH 6.5 phosphate buffer and from 4 to 24 hours the media was PH 7.5 phosphate buffer.

Alternatively, dissolution profiles are performed using a USP Type III (VanKel Bio-Dis II) apparatus.

Example 10

In vitro Fed/Fast Dissolution Protocol

The test formulations are evaluated under a variety of dissolution conditions to determine the effects of pH, media, agitation and apparatus. Dissolution tests are performed using a USP Type III (VanKel Bio-Dis II) apparatus. In order to determine the differences, if any, in dissolution kinetics between a fed state and a fasting state for the series of formulations, in vitro dissolution experiments are carried out in a solution containing 30% peanut oil ("fed") to model a gastrointestinal tract with a typical dietary fat load. The control determined the dissolution rates in a solution lacking the fat load ("fasted"). The pH-time protocol (ranging from acid to alkaline to model digestive processes) is set forth below in Table 10, below. Agitation is 15 cpm. Volume of the sample tested is 250 mL.

TABLE 10

Fed/Fast Dissolution Protocol

| Apparatus Media | | | |
| --- | --- | --- | --- |
| "Fed" | "Fasted" | Time | pH |
| 30% Peanut Oil | No Peanut oil | 0-1 hour | 1.5 |
| 30% Peanut Oil | No Peanut oil | 1-2 hour | 3.5 |
| 30% Peanut Oil | No Peanut oil | 2-4 hour | 5.5 |
| 30% Peanut Oil | No Peanut oil | 4-12 hour | 7.5 |

An enteric coating on the tablet is expected to provide a tablet that provides dissolution rates that are not significantly different in the fasted and fed states.

Example 11

In vitro Dose Scheduling Studies

Pharmacokinetic data (pk) data from human patients was used to model various dose regimens using human cell lines: Jurkat (leukemia) and HCT-116 (colon tumor). The human cell lines were treated with or without a HDAC inhibitor (e.g. Compound 1). Cells were cultured, treated according to different regimens and concentrations to model the corresponding dosing regimen (continuous low dose: 0.2 µM; intravenous (IV): 2 µM 3 hours+0.3 µM 4 hours; oral BID: 0.4 µM 4 hours×2, 4 hours apart; oral consecutive BID: 0.4 µM 8 hours; oral consecutive TID: 0.266 µM 12 hours), then washed out to mimic the human in vivo PK.

Figure 2:
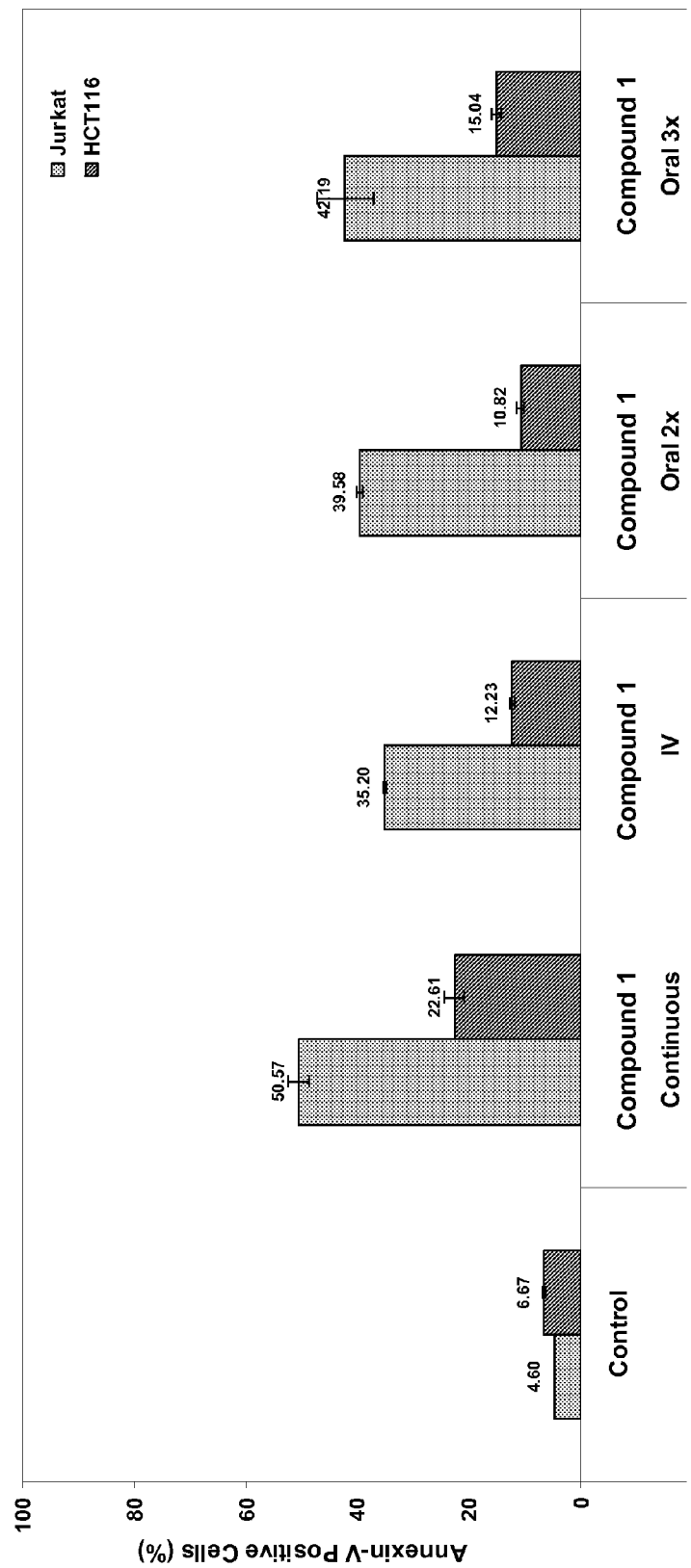
FIG. 2 presents the results of modeling dose schedules of Compound 1 and the effects on Jurkat and HCT116 cell lines.

FIGS. 1 and 2 summarize the results of the in vitro dose scheduling studies. It was determined that continuous exposure of the HDAC inhibitor for at least 8 hours provided good efficacy. Oral bid dosing is more efficacious when given consecutively (i.e. 4 hours apart) than with a break in between, similar to IV dosing modeled with a 8 h exposure. Oral three times a day dosing (tid) dosing was better than twice-a-day (bid) dosing, approaching the continuous 0.2 uM level.

Example 12

Phase 1 Trial of the Safety and Tolerability of Oral Capsule Form of Compound 1, HCl in Advanced Cancer Patients This is a Phase 1 dose-escalation study of the safety, pharmacokinetics, and pharmacodynamics of Compound 1, HCl administered orally in patients with advanced cancer.
Purpose
This study seeks to determine the highest dose of Compound 1, HCl that can be taken without causing serious side effects in patients with advanced cancer. The study will look at safety of the study drug (Compound 1, HCl) and whether the treatment schedule is tolerated by patients.
Study Design
In the Phase 1 dose escalation study, up to 7 cohorts will receive Compound 1, HCl orally at doses starting at 30 mg/m$^2$, approximately 4-6 hours apart, up to 90 mg/m$^2$, 2 or 3 times a day according to 3 different dosing schedules within 28 day cycle (5 days of dosing followed by 2 days of no dosing; 5 days of dosing followed by 9 days of no dosing; 7 days of dosing followed by 7 days of no dosing) until the maximum tolerated dose is reached.
Eligibility
Patients should satisfy the following criteria: At least 18 years of age; histologically confirmed, measurable solid tumor, non-Hodgkin's lymphoma, Hodgkin's disease, chronic lymphocytic leukemia, or multiple myeloma that has relapsed after standard therapy or for which no standard therapy exists; ability to swallow oral capsules without difficulty; estimated life expectancy>12 weeks; ECOG performance status≤2; Creatinine≤1.5×institutional upper limit of normal (ULN); Total bilirubin≤1.5×institutional ULN (unless elevated from documented Gilbert's syndrome); AST and ALT≤2.5×institutional ULN (≤5×institutional ULN in the presence of liver metastases); Platelet count≥100,000/4; ANC≥1500/μL; Hgb≥9.0 g/dL; Patients with previously treated, stable, asymptomatic brain metastases who are not on corticosteroids are eligible; Willing and able to sign a written informed consent.

Results

When delivered via an immediate release capsule formulation, therapeutic effect of Compound 1 was achieved with 2 or 3 consecutive doses (each dose administered 4 to 6 hours apart) on days scheduled for dosing. The doses were given at the same time each day. Over a daily exposure range of 0.63 to 2.15 μM·h, three-times-a-day (TID) consecutive dosing was associated with a higher average grade of thrombocytopenia when compared with twice a day (BID) consecutive dosing. When delivered via an immediate release capsule formulation, therapeutic effect of Compound 1 was achieved with 2 doses administered 4 to 6 hours apart on days scheduled for dosing. The two doses were given at the same time each day, with the second dose being administered approximately 4 to 6 hours from the first dose.

In solid tumor and lymphoma patients, a pharmacodynamic response to Compound 1 was achieved with limited incidence of Grade 4 thrombocytopenia (platelet count<25,000 per mm$^2$) when patients received drug in cycles consisting of 7 consecutive days of oral dosing followed by 7 consecutive days without dosing. In the event that a patient experiences a treatment-related decrease in platelets to <25,000 per mm$^2$, the severity of the thrombocytopenia may be ameliorated by dosing in cycles consisting 5 consecutive days of oral dosing followed by 9 consecutive days without dosing.

The following pharmacokinetic information was determined for patients that received a 30 mg/mm$^2$ dose of the capsule formulation of Example 2. Solid tumor cancer patients received a 30 mg/mm$^2$ dose of the capsule formulation of Example 2. Blood samples that were collected for up to 24 hours post-dosing were analyzed for pharmacokinetic evaluations. Plasma was harvested by centrifugation and stored at approximately −70° C. until analysis. Concentrations of Compound 1 were determined in plasma using HPLC gradient system (Hewlett Packard model 1100) was configured with Sciex API 3000 and a reversed phase column (Phenomenex, Luna C18, 3.0 μm, 50×2 mm i.d.). The mobile phase gradient consisted of 0.2% formic acid in water (A) and 0.2% formic acid in methanol (B). The flow rate was 0.4 mL/min, and run time was 2.75 minutes. Pharmacokinetic analysis was performed using WinNonlin Professional Edition (Pharsight Corporation, Version 5.2). Nominal sampling times and nominal dose levels were used. The $AUC_{0-4h}$ for plasma concentrations of Compound 1 was 0.272±0.051 μM·h (mean±SE).

The 95% confidence range for mean $AUC_{0-8h}$ at a dose of 60 mg/mm$^2$ is estimated to be 0.210 to 0.742 μM·h based on a single dosing of a 30 mg/mm$^2$ immediate release capsule formulation. The dose-normalized mean $AUC_{0-8h}$ for a once daily controlled release oral formulation is calculated to range from 0.0035 to 0.0124 (μM·h)/(mg/m$^2$).

Example 13

Combination Therapy: Bortezomib and Compound 1 in neuroblastoma in vitro and in vivo models Current treatment of neuroblastoma often fails due to chemo-resistance. The current study examined the effects of Compound 1 and the proteasome inhibitor, bortezomib in the treatment of neuroblastoma.

Neuroblastoma cell lines and patient-derived primary neuroblastoma cultures were treated with bortezomib, Compound 1 alone or a combination of both agents for 48 hours. Cells were also treated with HDAC inhibitors vorinostat, sodium butyrate, and valproic acid and viability was assessed by calcein AM assays. mRNA from treated cells was evaluated at 6 and 24 hours using U133+mRNA expression arrays and Ingenuity analysis. Dichlorofluorescein (DCF) was used to measure reactive oxygen species (ROS). Cell viability assays were repeated in the presence of N-acetylcysteine (NAC). Western blot evaluated caspase-3 and PARP cleavage. Nude mice were injected with 10$^7$ SMS-KCNR cells subcutaneously and treated with daily doses of 0.5 mg/kg bortezomib, 12.5 mg/kg Compound 1, or a combination of the two agents. Tumors were measured and imaged twice per week.

Neuroblastoma cell lines and patient cells showed sensitivity to bortezomib and Compound 1 with $IC_{50}$'s for bortezomib<50 nM and $IC_{50}$'s for Compound 1<200 nM. The combination of bortezomib and Compound 1 was synergistic. Expression analysis showed upregulation of NOTCH 2 and its ligands as well as c-jun. NFk-B and MYCN were both significantly down-regulated. DCF analysis showed formation of ROS and viability assays showed inhibition of caspase-mediated apoptosis in the presence of NAC. The neuroblastoma xenograft mouse model showed a decrease in tumor volume in mice treated with both bortezomib and Compound 1 when compared to the single agent treatment groups with significant survival benefit.

Bortezomib and Compound 1 synergistically inhibit neuroblastoma growth both in vitro and in vivo. This combination therapy is effective and well tolerated in the mouse model.

The examples and embodiments described herein are for illustrative purposes only and various modifications or changes suggested to persons skilled in the art are to be included within the spirit and purview of disclosure and scope of the appended claims. As will be appreciated by those skilled in the art, the specific components listed in the above examples may be replaced with other functionally equivalent components, e.g., diluents, binders, lubricants, fillers, coatings, and the like.

What is claimed is:

1. A method of treating cancer in a human, comprising: orally administering a first dose of Compound 1, and orally administering a second dose of Compound 1 about 4 to about 6 hours after the first dose Compound 1

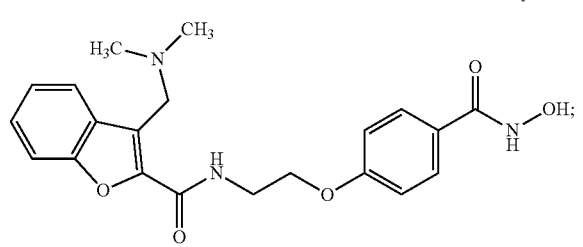

wherein a plasma concentration of Compound 1 which is effective for treating cancer is maintained for at least 6 consecutive hours.

2. The method of claim 1, wherein the effective plasma concentration of Compound 1 is about 0.2 uM.

3. The method of claim 1, wherein $AUC_{0-4h}$ of Compound 1 is about $0.272\pm0.051$ µM·h.

4. The method of claim 1, comprising orally administering a third dose of Compound 1, wherein the first dose, the second dose and the third dose are each administered 4 to 6 hours apart.

5. The method of claim 1, wherein the daily dose of Compound 1 is 2 mg/kg.

6. The method of claim 1, wherein the daily dose of is about 10 mg to about 300 mg.

7. The method of claim 1, wherein the cancer is a hematological cancer, solid tumor or a sarcoma.

8. The method of claim 1, wherein the cancer is selected from: breast cancer, colon cancer, colorectal carcinomas, non-small cell lung cancer, small-cell lung cancer, liver cancer, ovarian cancer, prostate cancer, uterine cervix cancer, urinary bladder cancer, gall bladder carcinoma, gastric carcinoma, esophageal cancer, gastrointestinal stromal tumor, pancreatic cancer, germ cell tumors, mast cell tumors, neuroblastoma, retinoblastoma, mesothelioma, mastocytosis, testicular cancers, glioblastomas, astrocytomas, sarcoma, osteosarcoma, B cell lymphoma, T cell lymphoma, NK cell lymphoma, Hodgkin's lymphoma, non-Hodgkin's lymphoma, melanoma, basal cell carcinoma, skin cancer, myeloma, leukemia, acute myelocytic leukemia (AML), acute lymphocytic leukemia (ALL), myelodysplastic syndrome, chronic lymphocytic leukemia (CLL) and chronic myelogenous leukemia (CML).

9. The method of claim 1, wherein the cancer is selected from: breast cancer, colon cancer, colorectal carcinomas, non-small cell lung cancer, liver cancer, ovarian cancer, uterine cervix cancer, gastric carcinoma, pancreatic cancer, glioblastomas, B cell lymphoma, T cell lymphoma, Hodgkin's lymphoma, non-Hodgkin's lymphoma, myeloma, myelodysplastic syndrome (MDS).

10. The method of claim 1, further comprising administering to the human at least one additional therapy selected from anti-cancer agents, anti-emetic agents, radiation therapy, or combinations thereof.

11. The method of claim 1, further comprising administering to the human at least one additional therapeutic agent selected from: DNA-damaging agents; topoisomerase I or II inhibitors; alkylating agents; PARP inhibitors; proteasome inhibitors; RNA/DNA antimetabolites; antimitotics; immunomodulatory agents; antiangiogenics; aromatase inhibitors; hormone-modulating agents; apoptosis inducing agents; kinase inhibitors; monoclonal antibodies; or combinations thereof.

12. The method of claim 1, further comprising administering to the human at least one additional therapeutic agent selected from: abarelix; ABT-888; aldesleukin; aldesleukin; alemtuzumab; alitretinoin; allopurinol; altretamine; amifostine anastrozole; arsenic trioxide; asparaginase; azacitidine; AZD-2281; arsenic trioxide; bendamustine; bevacizumab; bexarotene; bleomycin; bortezomib; BSI-201; busulfan; busulfan; calusterone; capecitabine; carboplatin; carfilzomib; carmustine; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine; denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzumab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; mechlorethamine; megestrol acetate; melphalan; mercaptopurine; methotrexate; methoxsalen; mitomycin C; mitomycin C; mitotane; mitoxantrone; nandrolone phenpropionate; nelarabine; NPI-0052; nofetumomab; oprelvekin; oxaliplatin; paclitaxel; paclitaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium; procarbazine; quinacrine; RAD001; rasburicase; rituximab; sargramostim; Sargramostim; sorafenib; streptozocin; sunitinib malate; tamoxifen; temozolomide; teniposide; testolactone; thalidomide; thioguanine; thiotepa; topotecan; toremifene; tositumomab; tositumomab/I-131 tositumomab; trastuzumab; tretinoin; uracil Mustard; valrubicin; vinblastine; vincristine; vinorelbine;vorinostat; zoledronate; zoledronic acid; vandetanib; lapatinib; nilotinib; axitinib; or combinations thereof.

13. The method of claim 1, further comprising administering to the human at least one additional therapeutic agent selected from: azacitidine; bendamustine; bevacizumab; bleomycin; bortezomib; carboplatin; chlorambucil; cisplatin; cyclophosphamide; cytarabine; dacarbazine; darbepoetin alfa; daunorubicin liposomal; daunorubicin; decitabine; docetaxel; doxorubicin; doxorubicin liposomal; epirubicin; epoetin alfa; erlotinib; etoposide; fludarabine; fluorouracil; gemcitabine; Ibritumomab tiuxetan; irinotecan; lenalidomide; leucovorin; melphalan; methotrexate; oxaliplatin; paclitaxel; paclitaxel protein-bound particles; pemetrexed disodium; pentostatin; RAD001; rituximab; sorafenib; sunitinib malate; tamoxifen; temozolomide; topotecan; tositumomab; tositumomab/I-131 tositumomab; trastuzumab; vincristine; vinorelbine; or combinations thereof.

* * * * *

UNITED STATES PATENT AND TRADEMARK OFFICE
CERTIFICATE OF CORRECTION

| | |
|---|---|
| PATENT NO. | : 8,603,521 B2 |
| APPLICATION NO. | : 12/761588 |
| DATED | : December 10, 2013 |
| INVENTOR(S) | : David J. Loury et al. |

It is certified that error appears in the above-identified patent and that said Letters Patent is hereby corrected as shown below:

In the Specification

Column 48, line 39, replace "continuous 0.2uM level" with --continuous 0.2µM level--

In the Claims

Column 51, line 18, claim 2, replace "Compound 1 is about 0.2 uM" with --Compound 1 is about 0.2 µM--

Column 51, lines 26-27, claim 6, replace "wherein the daily dose of is about 10 mg to about 300 mg" with --wherein the daily dose of Compound 1 is about 10 mg to about 300 mg--

Column 51, lines 51-52, claim 9, replace "myeloma, myelodysplastic syndrome (MDS)." with --myeloma and myelodysplastic syndrome (MDS).--

Column 52, lines 8-37, claim 12, replace:
"aldesleukin; aldesleukin; alemtuzumab; alitretinoin; allopurinol; altretamine; amifostine anastrozole; arsenic trioxide; asparaginase; azacitidine; AZD-2281; arsenic trioxide; bendamustine; bevacizumab; bexarotene; bleomycin; bortezomib; BSI-201; busulfan; busulfan; calusterone; capecitabine; carboplatin; carfilzomib; carmustine; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine;

Signed and Sealed this
Tenth Day of June, 2014

Michelle K. Lee
*Deputy Director of the United States Patent and Trademark Office* denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzumab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; meclorethamine; megestrol acetate; melphalan; mercaptopurine; methotrexate; methoxsalen, mitomycin C; mitomycin C; mitotane; mitoxantrone; nandrolone phenpropionate; nelarabine; NPI-0052; nofetumomab; oprelvekin; oxaliplalin; paclitaxel; pachtaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium; procarbazine; quinacrine; RAD001; rasburicase; rituximab; sargramostim; Sargramostim"

with:

--aldesleukin; alemtuzumab; alitretinoin; allopurinol; altretamine; amifostine anastrozole; arsenic trioxide; asparaginase; azacitidine; AZD-2281; bendamustine; bevacizumab; bexarotene; bleomycin; bortezomib; BSI-201; busulfan; calusterone; capecitabine; carboplatin; carfilzomib; carmustine; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunorubicin liposomal; daunorubicin; decitabine; denileukin; dexrazoxane; docetaxel; doxorubicin; doxorubicin liposomal; dromostanolone propionate; epirubicin; epoetin alfa; erlotinib; estramustine; etoposide phosphate; etoposide; exemestane; filgrastim; floxuridine; fludarabine; fluorouracil; fulvestrant; gefitinib; gemcitabine; gemtuzumab ozogamicin; goserelin acetate; histrelin acetate; hydroxyurea; Ibritumomab tiuxetan; idarubicin; ifosfamide; imatinib mesylate; interferon alfa 2a; Interferon alfa-2b; irinotecan; lenalidomide; letrozole; leucovorin; leuprolide Acetate; levamisole; lomustine; mechlorethamine; megestrol acetate; melphalan; mercaptopurine; methotrexate; methoxsalen; mitomycin C; mitotane; mitoxantrone; nandrolone phenpropionate; nelarabine; NPI-0052; nofetumomab; oprelvekin; oxaliplatin; paclitaxel; paclitaxel protein-bound particles; palifermin; pamidronate; panitumumab; pegademase; pegaspargase; pegfilgrastim; pemetrexed disodium; pentostatin; pipobroman; plicamycin, mithramycin; porfimer sodium; procarbazine; quinacrine; RAD001; rasburicase; rituximab; sargramostim--